US008455220B2

(12) United States Patent
Jalan et al.

(10) Patent No.: US 8,455,220 B2
(45) Date of Patent: Jun. 4, 2013

(54) BIOMARKERS FOR ASSESSING LIVER FUNCTION

(75) Inventors: Rajiv Jalan, London (GB); Rajeshwar P Mookerjee, London (GB); Nathan Davies, London (GB)

(73) Assignee: UCL Business PLC, London (GB)

( * ) Notice: Subject to any disclaimer, the term of this patent is extended or adjusted under 35 U.S.C. 154(b) by 771 days.

(21) Appl. No.: 12/440,170

(22) PCT Filed: Sep. 7, 2007

(86) PCT No.: PCT/GB2007/003362
§ 371 (c)(1),
(2), (4) Date: Jun. 19, 2009

(87) PCT Pub. No.: WO2008/029145
PCT Pub. Date: Mar. 13, 2008

(65) Prior Publication Data
US 2009/0280519 A1    Nov. 12, 2009

(30) Foreign Application Priority Data
Sep. 7, 2006    (GB) .................................. 0617581.4

(51) Int. Cl.
*C12P 21/04* (2006.01)
(52) U.S. Cl.
USPC ........................................ 435/69.6; 424/520
(58) Field of Classification Search
USPC ........................................ 435/69.6; 424/520
See application file for complete search history.

(56) References Cited

U.S. PATENT DOCUMENTS
2002/0081626 A1    6/2002  Kaddurah-Daouk et al.

FOREIGN PATENT DOCUMENTS
| WO | WO 97/34605 | 9/1997 |
| WO | WO 02/04465 A1 | 1/2002 |
| WO | WO 2004/046314 A2 | 6/2004 |
| WO | WO 2004/012686 A2 | 12/2004 |
| WO | WO 2005/039598 A1 | 5/2005 |

OTHER PUBLICATIONS

Siroen et al. "The transplanted liver graft is capable of clearing asymmetric dimethylarginine", Liver Transplantation, 2004, 10(12):1524-1530.*
Zapico-Muniz et al. "Ischemia-modified albumin during skeletal muscle ischemia", Clinical Chemistry, 2004, 50(6):1063-1065.*
Apple et al. "Future biomarkers for detection of ischemia and risk stratification in acute coronary syndrome", Clinical Chemistry, 2005, 51(5):810-824.*
Siroen et al. "The human liver clears both asymmetric and symmetric dimethylarginine", Hepatology, 2005, 41:559-565.*
Kamath et al. "A model to predict survival in patients with end-stage liver disease", Hepatology, 2001, 33:464-470.*
Bentancur et al., "Comprehensive Study of Myocarditis in the Emergency Department (COSMED V): Endothelial Activation, Oxygen Stress, and NT-proBNP in Acute Myocarditis," Annals of Emergency Medicine, vol. 50, No. 3, p. S72 (2007), (Abstract).
Mookerjee et al., "Dimethylarginine (NOS Inhibitor) Levels Predict In-Patient Mortality in Alcoholic Hepatitis," Hepatoligy, vol. 42, No. 4, Suppl. 1, p. 493A (2005), (Abstract).
Carrega et al., "Influence of the Dialysis Membrane on Markers of Tissue Ischemia," Journal of Investigative Medicine, vol. 54, No. 2, pp. 62-66 (2006).
Al-Saad et al., "Ischemia Modified Albumin Characterized and Determined by Mass Spectrometry," Proceedings 50th ASMS Conference on Mass Spectrometry and Allied Topics; Proceedings—50th ASMS Conference on Mass Spectrometry and Allied Topics (2002), (Abstract).
Carnegie et al., "Urinary Excretion of Methylarginine in Human Disease," Metabolism, vol. 26, No. 5, pp. 531-537 (1977).
Zoccali et al., "Plasma Concentration of Asymmetrical Dimethylarginine and Mortality in Patients with End-Stage Renal Disease: A Prospective Study," The Lancet, vol. 358, pp. 2113-2117 (2001).
Mookerjee et al., "Increasing Dimethylargine Levels Are Associated with Adverse Clinical Outcome in Severe Alcoholic Hepatitis," Hepatology, vol. 45, No. 1, pp. 62-71 (2007).
Lluch et al., "Plasma Concentrations of Nitric Oxide and Asymmetric Dimethylarginine in Human Alcoholic Cirrhosis," Journal of Hepatology 41, pp. 55-59 (2004).
International Search Report for PCT/GB2007/003362 completed Nov. 9, 2007, 6 pgs.
Written Opinion of the International Searching Authority for PCT/GB2007/003362 completed Nov. 9, 2007, 12 pgs.
Apple et al., "Future Biomarks for Detection of Ischemia and Risk Stratification in Acute Coronary Syndrome," Clinical Chemistry, vol. 51, No. 5, pp. 810-824 (2005).
Tome et al., "Review article: Current Management of Alcoholic Liver Disease," Aliment Pharmacol Ther., vol. 19, pp. 707-714 (2004).
Duvoux et al., "Low-Grade Steatosis and Major Changes in Portal Flow as New Prognostic Factors in Steroid-Treated Alcoholic Hepatitis," Hepatology, vol. 40, No. 6, pp. 1370-1378 (2004).
Ripoll et al., "Influence of Hepatic Venous Pressure Gradient on the Prediction of Survival of Patients with Cirrhosis in the MELD Era," Hepatology, vol. 42, No. 4, pp. 793-801 (2005).
Wiest et al., "The Paradox of Nitric Oxide in Cirrhosis and Portal Hypertension: Too Much, Not Enough," Hepatology, vol. 35, pp. 478-491 (2002).
Gupta et al., "Endothelial Dysfunction and Decreased Production of Nitric Oxide in the Intrahepatic Microcirculation of Cirrhotic Rats," Hepatology, vol. 28 pp. 926-931 (1998).
Rockey et al., "Reduced Nitric Oxide Production by Endothelial Cells in Cirrhotic Rat Liver: Endothelial Dysfunction in Portal Hypertension," Gastroenterology, pp. 344-351 (1998).
Fiorucci et al., "NCX-1000, a Nitric Oxide-Releasing Derivative of Ursodeoxycholic Acid, Ameliorates Portal Hypertension and Lowers Norepinephrine-Induced Intrahepatic Resistance in the Isolated and Perfused Rat Liver," *J. Hepatology*, vol. 39, pp. 932-939 (2003).

(Continued)

*Primary Examiner* — Susan Hanley
*Assistant Examiner* — Bin Shen
(74) *Attorney, Agent, or Firm* — Foley & Lardner LLP

(57) ABSTRACT

A method for assessing liver function in an individual, which method comprises determining the level of methylarginine(s) (such as ADMA and/or SDMA) and the ratio of ischemia modified albumin (IMA): albumin ratio (IMAR) in the individual, thereby to assess liver function in the individual.

10 Claims, 11 Drawing Sheets

OTHER PUBLICATIONS

Van De Casteele et al., "In Vivo Gene Transfer of Endothelial Nitric Oxide Synthase Decreases Portal Pressure in Anaesthetised Carbon Tetrachloride Cirrhotic Rats," *Gut Journ.*, vol. 51, pp. 440-445 (2002).

Shah et al., "Gene Transfer of Recombinant Endothelial Nitric Oxide Synthase to Liver in Vivo and in Vitro," *Am. J. Physiol. Gastrointest Liver Physiol.*, vol. 279, pp. G1023-G1030 (2000).

Morales-Ruiz et al., "Transduction of the Liver with Activated Akt Normalizes Portal Pressure in Cirrhotic Rats," *Gastroenterology*, vol. 125, pp. 522-531 (2003).

Leiper et al., "Biological Significance of Endogenous Methylarginines that Inhibit Nitric Oxide Synthases," *Cardiovasc. Res.*, vol. 43, pp. 542-548 (1999).

MacAllister et al., "Regulation of Nitric Oxide Synthesis by Dimethylarginine Dimethylaminohydrolase," *British J. Pharmacol.*, vol. 119, pp. 1533-1540 (1996).

Nijveldt et al., "The Liver is an Important Organ in the Metabolism of Asymmetrical Dimethylarginine (ADMA)," *Clinical Nutrition*, vol. 22, pp. 17-22 (2003).

Siroen et al., "The Transplanted Liver Graft is Capable of Clearing Asymmetric Dimethylarginine," *Liver Transplantation*, vol. 10, pp. 1524-1530 (2004).

Nijveldt et al., "Asymmetrical Dimethylarginine (ADMA) in Critically Ill Patients: High Plasma ADMA Concentration is an Independent Risk Factor of ICU Mortality," *Clin. Nutr.*, vol. 22, No. 1, pp. 23-30 (2003).

Ito et al., "Novel Mechanism for Endothelial Dysfunction: Dysregulation of Dimethylarginine Dimethylaminohydrolase," *Circulation*, vol. 99, pp. 3092-3095 (1999).

MacSween et al., "Histologic Spectrum of Alcoholic Liver Disease," *Semin. Liver Dis.*, vol. 6, pp. 221-232 (1986).

Bone et al., "The ACCP-SCCM Consensus Conference on Sepsis and Organ Failure," vol. 101, No. 6, *Chest*, pp. 1481-1483 (1992).

Owen et al., "Validation of a Liquid Chromatography Tandem Mass Spectrometry Assay for Serum Creatinine and Comparison with Enzymatic and Jaffe Methods," *Ann. Clin. Biochem.*, vol. 43, pp. 118-123 (2006).

Tilg et al., Anti-Tumor Necrosis Factor-Alpha Monoclonal Antibody Therapy in Severe Alcoholic Hepatitis. *J. Hepatol.*, vol. 38, pp. 419-425 (2003).

Gornall et al., "Determination of Serum Proteins by Means of the Biuret Reaction," *J. Biol. Chem.*, vol. 177, pp. 751-766 (1948).

Infante-Rivard et al., "Clinical and Statistical Validity of Conventional Prognostic Factors in Predicting Short-Term Survival Among Cirrhotics," *Hepatology*, vol. 7, pp. 660-664 (1987).

Kamath et al., "A Model to Predict Survival in Patients with End-Stage Liver Disease," *Hepatology*, vol. 33, pp. 464-470 (2001).

Brunt et al., "Nonalcoholic Steatohepatitis: a Proposal for Grading and Staging the Histological Lesions," *Am. J. Gastroenterol.*, vol. 94, pp. 2467-2474 (1999).

Maddrey et al., "Corticosteroid Therapy of Alcoholic Hepatitis," *Gastroenterology*, vol. 75, pp. 193-199 (1978).

Tsikas et al., "Elevated Plasma and Urine Levels of ADMA and 15(S)-8-iso-PGF$_{2\alpha}$ in End-Stage Liver Disease," *Hepatology*, vol. 38, pp. 1063-1064 (2003).

Khoruts et al., "Circulating Tumor Necrosis Factor, Interleukin-1 and Interleukin-6 Concentrations in Chronic Alcoholic Patients," *Hepatology*, vol. 13, pp. 267-276 (1991).

Lopez-Talavera et al., "Tumor Necrosis Factor Alpha: a Major Contributor to the Hyperdynamic Circulation in Prehepatic Portalhypertensive Rats," *Gastroenterology*, vol. 108, pp. 761-767 (1995).

Iimuro et al., "Antibodies to Tumor Necrosis Factor Alfa Attenuate Hepatic Necrosis and Inflammation Caused by Chronic Exposure to Ethanol in the Rat," *Hepatology*, vol. 26, pp. 1530-1537 (1997).

Austin et al., "A Pilot Study to Investigate the Use of Oxpentifylline (Pentoxifylline) and Thalidomide in Portal Hypertension Secondary to Alcoholic Cirrhosis," *Aliment Pharmacol. Ther.*, vol. 19, pp. 79-88 (2004).

Lopez-Talavera et al., "Thalidomide Inhibits Tumor Necrosis Factor Alpha, Decreases Nitric Oxide Synthesis, and Ameliorates the Hyperdynamic Circulatory Syndrome in Portalhypertensive Rats," *Hepatology*, vol. 23, pp. 1616-1621 (1996).

Mookerjee et al., "Tumor Necrosis Factor $\alpha$ is an Important Mediator of Portal and Systemic Haemodynamic Derangements in Alcoholic Hepatitis," *Gut*, vol. 52, pp. 1182-1187 (2003).

Achan et al., "Asymmetric Dimethylarginine Causes Hypertension and Cardiac Dysfunction in Humans and is Actively Metabolized by Dimethylarginine Dimethylaminohydrolase," *Arterioscler Thromb. Vasc. Biol.*, vol. 23, pp. 1455-1459 (2003).

Savvidou et al., "Endothelial Dysfunction and Raised Plasma Concentrations of Asymmetric Dimethylarginine in Pregnant Women who Subsequently Develop Preeclampsia," *Lancet*, vol. 361, pp. 1511-1517 (2003).

Jalan et al., "Liver Derived Proinflammatory Cytokines may be Important in Producing Intracranial Hypertension in Acute Liver Failure," *J. Hepatology*, vol. 37, pp. 536-538 (2002).

Ogawa et al., "Occurrence of a New Enzyme Catalyzing the Direct Conversion of $N^G,N^G$-Dimethyl-L-Arginine to L-Citrulline in Rats," *Biochem. Biophys. Res. Commun.*, vol. 148, No. 2, pp. 671-677 (1987).

McBride et al., "State of the Arg: Protein Methylation at Arginine Comes of Age," *Cell*, vol. 106, pp. 5-8 (2001).

Marliss et al., "Elevations of Plasma Methylarginines in Obesity and Ageing are Related to Insulin Sensitivity and Rates of Protein Turnover," *Diabetologia*, vol. 49, pp. 351-359 (2006).

Inoue et al., "Decrease of 3-Mmethylhistidine and Increase of $N^G,N^G$-Dimethylarginine in the Urine of Patients with Muscular Dystrophy," *Metabolism*, vol. 28, pp. 801-804 (1979).

Böger et al., "LDL Cholesterol Upregulates Synthesis of Asymmetrical Dimethylarginine in Human Endothelial Cells: Involvement of Sadenosylmethionine-Dependent Methyltransferases," *Circ. Res.*, vol. 87, pp. 99-105 (2000).

Akriviadis et al., "Pentoxifylline Improves Short-Term Survival in Severe Acute Alcoholic Hepatitis: a Doubleblind, Placebo-Controlled Trial," *Gastroenterology*, vol. 119, pp. 1637-1648 (2000).

Carithers et al., "Methylprednisolone Therapy in Patients with Severe Alcoholic Hepatitis: A Randomized Multicenter Trial.," *Ann. Intern. Med.*, vol. 110, pp. 685-690 (1989).

Forrest et al., "Analysis of Factors Predictive of Mortality in Alcoholic Hepatitis and Derivation and Validation of the Glasgow Alcoholic Hepatitis Score," *Gut*, vol. 54, pp. 1174-1179 (2005).

Dunn et al., "MELD Accurately Predicts Mortality in Patients with Alcoholic Hepatitis," *Hepatology*, vol. 41, pp. 353-358 (2005).

Kielstein et al., "Effects of Asymmetric Dimethylarginine (ADMA) Infusion in Humans," *Eur. J. Clin. Pharmacol.*, vol. 62, Suppl. 13, pp. 39-44 (2006).

Lluch et al., "Accumulation of Symmetric Dimethylarginine in Hepatorenal Syndrome," *Exp. Biol. Med.* (Maywood), vol. 231, pp. 70-75 (2006).

Mookerjee, et al., "Hepatic Inflammation Increase Portal Pressure Through Inhibition of Enos Activity: Potential Mechanisms", GUT abstracts, Apr. 2006, vol. 55, Supp2.

* cited by examiner (a)
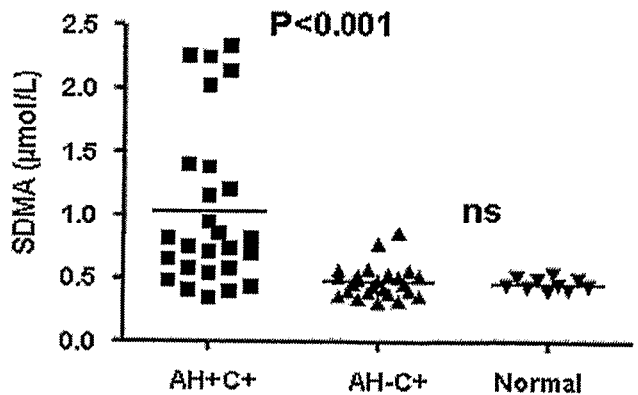
(b)
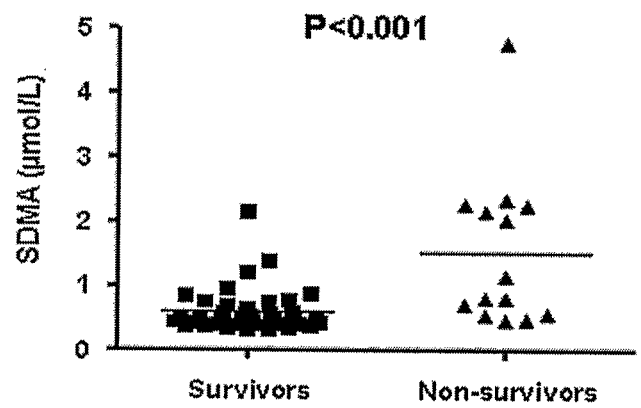
(c)
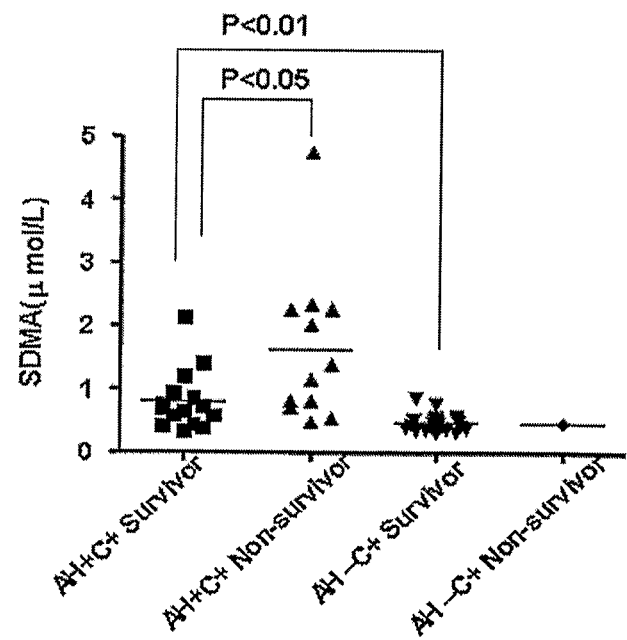
Figure. 2

IMAR
AUROC: 0.73 (±0.06)
DASIMAR
AUROC: 0.91 (±0.04)
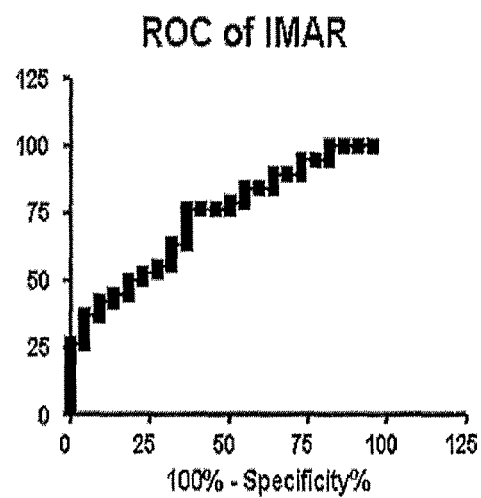
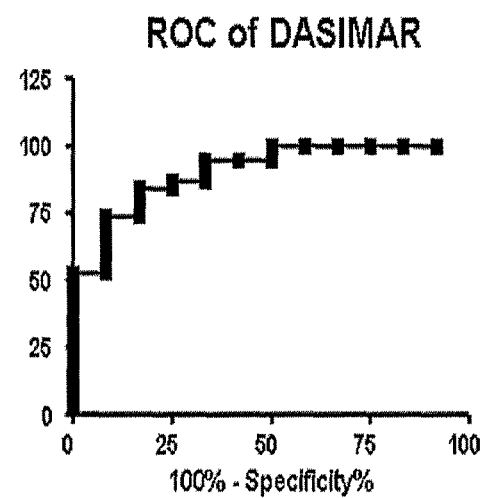
Figure. 9

BIOMARKERS FOR ASSESSING LIVER FUNCTION

CROSS-REFERENCE TO RELATED APPLICATIONS

This application is the U.S. National Phase of International Patent Application No. PCT/GB2007/003362, filed Sep. 7, 2007, which was published in English as WO 2008/029145 on Mar. 13, 2008, and claims priority under 35 U.S.C. §119 to Great Britain Patent Application No. GB 0617581.4, filed Sep. 7, 2006. The contents of these applications are incorporated herein by reference in their entirety.

FIELD OF THE INVENTION

The invention relates to a method for assessing liver function, in particular for predicting the clinical outcome of liver disease. It also relates to a kit for use in such a method and to the treatment of an individual identified as at risk of deleterious outcome using the method.

BACKGROUND TO THE INVENTION

Statistics from the NIH suggest there are in excess of 3000 patients with fulminant hepatic failure per year in the United States. If this data is extrapolated to incorporate the increasing burden of viral and alcoholic liver disease in The West and also in the under-developed world, the number of cases exceeds millions per year world-wide.

With global increasing incidence of end-stage liver disease secondary to alcohol injury, viral hepatitis and the more recently identified entity of non-alcoholic fatty liver disease, and a lack of significant increase in the liver transplant donor pool, a need for identification of individuals with rapid deterioration in liver function requiring supportive and interventional treatments, has markedly increased.

SUMMARY OF THE INVENTION

The inventors examined decompensated alcoholic cirrhosis patients and have established that plasma levels of two methylarginines in plasma, asymmetric dimethylarginine (ADMA) and its stereo-isomer symmetric dimethylarginine (SDMA), are significantly higher in alcoholic hepatitis patients and in non-survivors.

The combined sum of plasma ADMA and SDMA, termed a dimethylarginine score (DAS), was also a better predictor of clinical outcome in alcoholic cirrhotic patients than other known biological scoring systems or either dimethylarginine alone.

Accordingly, elevated levels of methylarginines represent important biological markers of deleterious outcome in alcoholic hepatitis patients, in whom there is also a high incidence of organ failure and sepsis. These markers may be used as a reliable predictor of progression and outcome in patients with liver disease, those undergoing liver transplantation and in patients with multi-organ failure and sepsis.

The inventors have established further that, in patients with alcoholic liver disease, patients who die have a significantly increased ischemia modified albumin (IMA):albumin ratio (or "IMAR").

Despite methylarginine levels, DAS and IMAR being suggestive of markers for disease progression and outcome, the inventors have found that combining methylarginine measurement with IMAR as a combined biomarker improves the predictive utility of poor outcome and, therefore, that such a combination provides a predictive utility to assess mortality risk. In particular, the inventors have found that combining DAS with IMAR as a combined biomarker ("DASIMAR") provides an excellent predictive utility to assess mortality risk.

In accordance with the present invention, there is thus provided a method for assessing liver function in an individual, which method comprises determining the level of one or more methylarginines and the ratio of ischemia modified albumin (IMA):albumin ratio (IMAR) in the individual.

The invention also provides:
  a test kit suitable for use in a method for predicting the outcome of liver disease in an individual, which test kit comprises means for determining the level of one or more methylarginines and/or the ratio of ischemia modified albumin (IMA):albumin ratio (IMAR) in the individual;
  use of an agent in the manufacture of a medicament for use in a method of treatment of liver disease in an individual, wherein the individual has been identified as having an increased risk of mortality according to the method of the invention;
  a method for the treatment of liver disease in an individual, which method comprises:
    (i) determining whether the individual has an increased risk of death using a method according to the invention; and
    (ii) administering to a individual identified in (i) as at risk of death, a therapeutically effective amount of an agent useful in the treatment of liver disease; and
  products containing:
    (i) means for determining the level of one or more methylarginines and the ratio of ischemia modified albumin (IMA):albumin ratio (IMAR) in the individual; and
    (ii) an agent which is useful in the treatment of liver disease, as a combined preparation for simultaneous, separate or sequential use in a method of treatment of the human or animal body by therapy.

BRIEF DESCRIPTION OF THE DRAWINGS

FIG. 2 shows SDMA levels in patients and healthy volunteers: (a) AH+C+ patients have significantly higher SDMA levels (P<0.001) compared to AH−C+ patients. There was no difference in SDMA levels between AH−C+ patients and healthy volunteers. (b) In-patient survivors with decompensated cirrhosis (n=39) had significantly lower SDMA levels than those that died (n=13); P<0.001. (c) Sub-analysis of patients demonstrated greater SDMA levels in AH+C+ patients that died (n=12) compared with AH+C+ survivors; P<0.01. AH+C+ survivors (n=15) also had higher SDMA values compared with AH−C+ (non-inflammatory cirrhotic) survivors (n=24); P<0.01.

FIG. 9 shows survival receiver operator curves are for IMAR and DASIMAR, respectively. It can be seen that the predictive utility is greater for DASIMAR than IMAR alone, which we suggest relates to the synergistic and additional contributions to the pathology of summing the two predictive scores, DAS and IMAR, reflecting inflammation and hemodynamic changes in addition to progressive severity of liver dysfunction, as liver and multi-organ failure evolves.

DETAILED DESCRIPTION OF THE INVENTION

Throughout this specification, the word "comprise", or variations such as "comprised" or "comprising", will be understood to imply the inclusion of a stated element, integer or step, or group of elements, integers or steps, but not the exclusion of any other element, integer or step, or group of elements, integers or steps.

The reference to any prior art in this specification is not, and should not be taken as, an acknowledgement or any form of suggestion that that prior art forms part of the general knowledge in Australia or elsewhere.

Currently used prognostic scores for liver failure lack specificity, which partly relates to the use of clinical variables which are subject to observer differences. These scores also incorporate biological parameters such as bilirubin and prothrombin time, the assays for which vary between laboratories, whilst other biological parameters such as creatinine are affected by nutritional status and cholestosis in patients with progressive liver injury.

There is thus a need to find a specific and sensitive marker of progressive liver dysfunction that remains independent of clinical and biological variables, which are subject to variation dependent on patient and lab status. This marker should also reflect the evolution of pathology, with specific reference to inflammation and organ dysfunction.

The present invention is based on a combination of two types of markers, methylarginines and ischemia modified albumin (IMA).

There are two methylated arginines in plasma, asymmetric dimethylarginine [ADMA] and its stereo-isomer symmetric dimethylarginine [SDMA]. Measurement of methylarginine in accordance with the invention may encompass the measurement of one or more methylarginines such as one or both of these dimethylarginines. For example, in one embodiment, measurement of methylarginine in accordance with the invention may be measurement of combined ADMA and SDMA, giving a combined dimethylarginine score (DAS).

The inventors have determined that the measurement of dimethylarginines, products of normal post-translational protein modifications, using a combined dimethylarginine score (DAS score) allows the shortcomings of currently used biological scoring systems to be overcome, whilst also reflecting the evolution of pathology with a reliable predictive utility of early (28 day) mortality form liver failure, as demonstrated in a recent pilot study.

Figure 1:
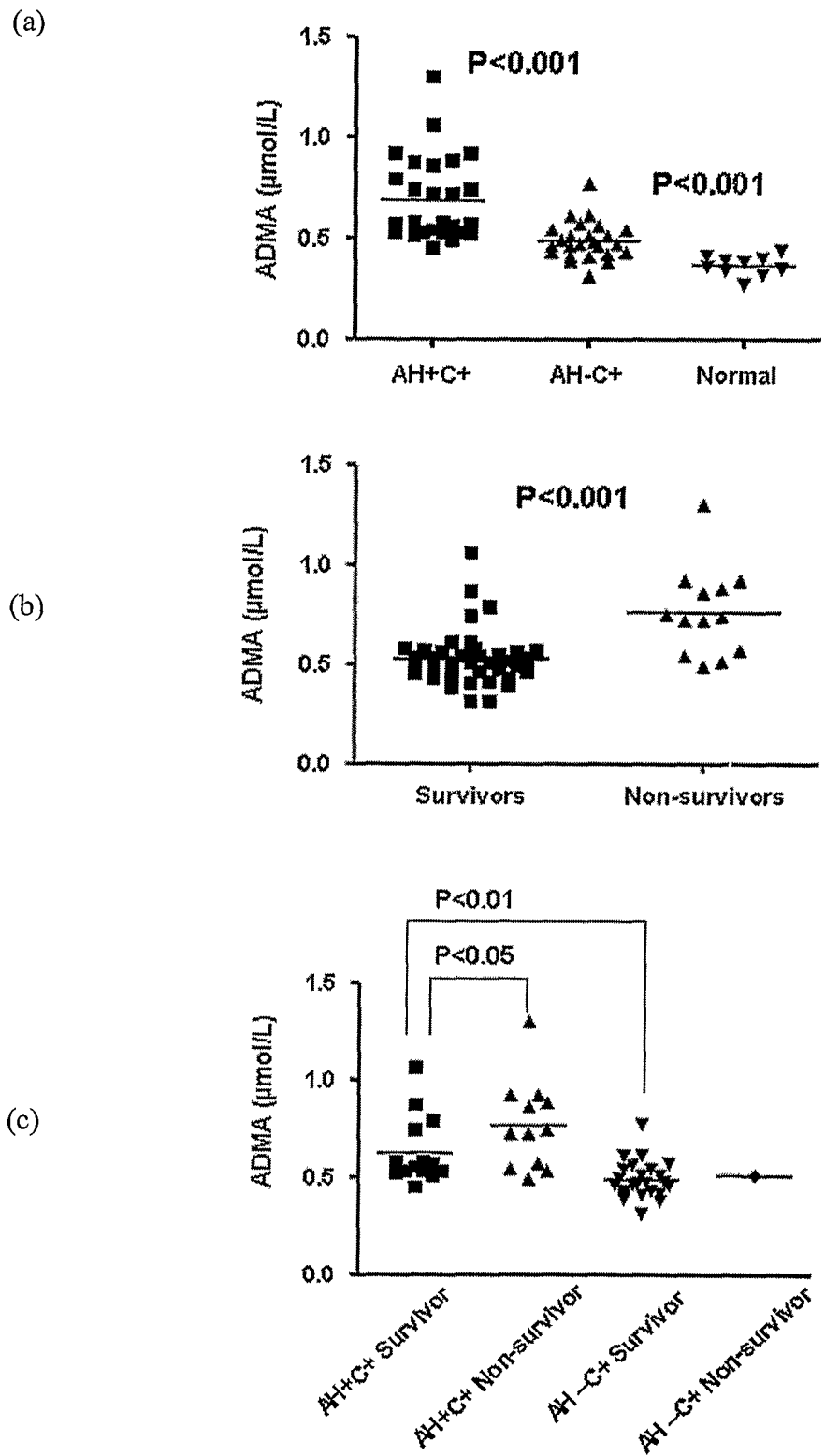
FIG. 1 shows ADMA levels in patients and healthy volunteers: (a) Patients with cirrhosis with superadded alcoholic hepatitis (AH+C+) have significantly higher ADMA levels (P<0.001) compared to patients with cirrhosis alone (AH−C+). All cirrhotic patients had significantly higher ADMA levels compared with normal volunteers (P<0.001). (b) In-patient survivors with decompensated cirrhosis (n=39) had significantly lower ADMA levels than those that died (n=13); P<0.001. (c) Sub-analysis of patients demonstrated greater ADMA levels in AH+C+ survivors (n=15) compared with AH−C+ survivors (n=24); P<0.01. ADMA levels were higher in AH+C+ patients that died (n=12) compared with AH+C+ survivors; P<0.05)
Figure 4:
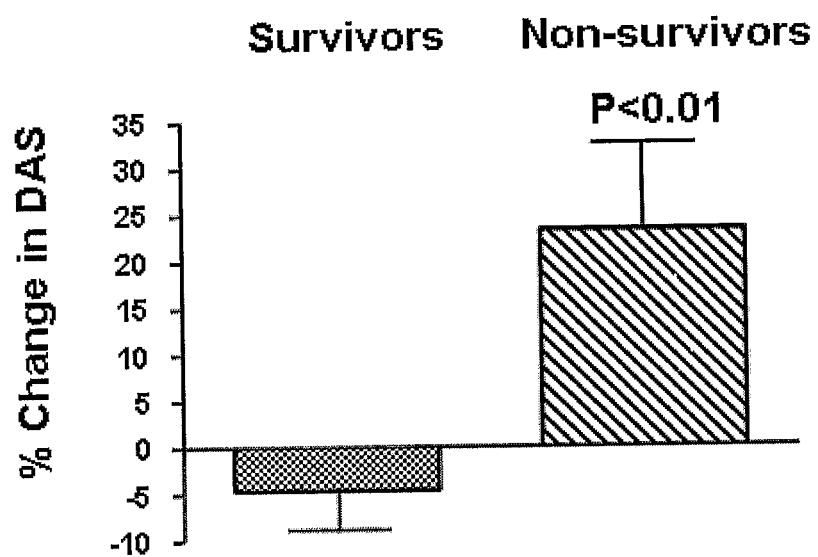
FIG. 4 shows percentage change in dimethylarginine score (DAS) during the course of admission in survivors and non-survivors. This figure shows the percentage increase in DAS [ADMA+SDMA] value in non-surviving AH+C+ patients (n=12) compared to values from 18 surviving patients, including 6 AH+C+ patients, in whom there was a net decrease in DAS value (P<0.01).

A DAS score is calculated from the summation of measured values of ADMA and SDMA. The inventors' studies suggest that these two variables reflect both inflammatory status and identify early evolution of organ failure (FIG. 1). Furthermore, patients that die have a significant percentage increase in DAS compared with survivors, in whom there is a relative reduction (FIG. 4).

The inventors have demonstrated that the use of these measurements acts as a reliable predictor of outcome in patients with acute liver failure, including changes with liver transplantation, as well as in those with ACLF. It is believed that application of this test or score helps define those patients with progressive liver failure in whom early intervention with liver support systems is warranted, compared with currently available prognostic scores (DF, MELD, Child-Pugh). (see FIG. 6: ROC curves).

Its use may also be extended to (i) a population of patients awaiting transplantation to stratify utilization of organs for transplantation or to determine organ function after orthotopic liver transplantation (ii) patient with multi-organ failure and sepsis with liver dysfunction, in which a method as described herein, such as a method that assesses the combined DAS value, could be used to predict poor outcome.

The potential advantages of the methylarginine or DAS score system is that it involves a highly precise measurement of ubiquitous methylarginines that are not dependent on nutritional intake (as creatinine is) nor variations of assays across continents as occurs with the use of Prothrombin Time measurement applied to current scoring systems. DAS measurement is also not dependent on clinical variables and its mathematical calculation can be derived at the bedside, without the need for computation. The currently validated measurement systems include the use of high-performance liquid chromatography or/and mass-spectrometry to achieve reproducible and reliable separations between the stereoisomers. However, a methylarginine measurement or a DAS score may be determined using any suitable method, for example in the form of an assay which could be performed at the bedside, using an ELISA which would simplify measurement within a clinical setting.

Figure 8:
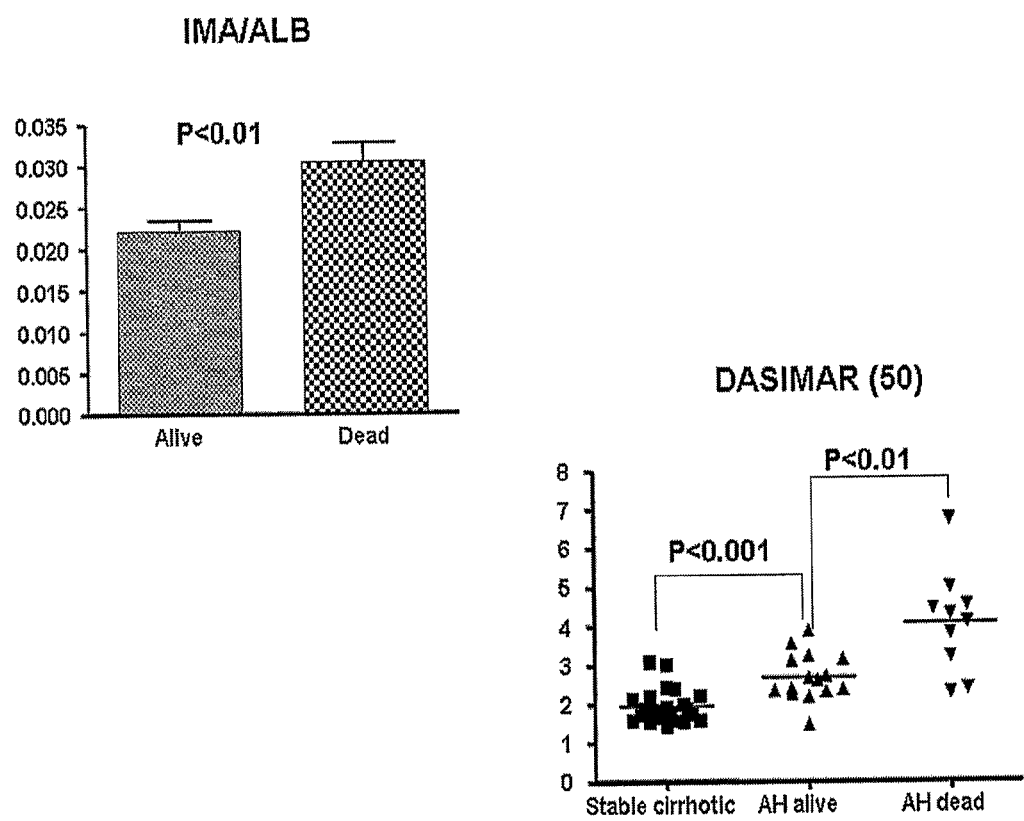
FIG. 8 shows that decompensated alcoholic FIG. 8 demonstrates that decompensated alcoholic cirrhotic patients who die have a significantly increased IMA/Alb ratio, compared to survivors, likely to reflect the worsening in disease severity and the higher index of inflammation in these patients. This point is illustrated in the lower panel where it can be seen that patients with the additional inflammatory component of alcoholic hepatitis (AH) have a higher DAS and IMAR than stable cirrhotics; Survivors of AH have lower DASIMAR scores than those that die with progression of their disease.

Given that the varying levels of albumin in liver patients determined partly by nutrition and largely by residual liver synthetic function, the inventors have modified the application of the albumin-cobalt binding assay to factor in a ratio of IMA to native albumin in the serum—a serum IMA:albumin ratio, or "IMAR". Data in a series of 52 decompensated patients with alcoholic liver disease suggest that patients who die have a significantly increased IMA:albumin ratio ($P<0.01$). Furthermore, as with the methylarginine or DAS value, there is a suggestion that IMAR may reflect inflammatory status and thereby the underlying pathological evolution of the disease (see FIG. 8). Using receiver operator curves to predict mortality, the area under the curve was found to be 0.73 (±0.06) for the cohort studied, suggesting that IMAR may be a useful predictive test of mortality in these patients.

However, the inventors have found that a combination of a methylarginine measurement (such as DAS) with IMAR as a combined biomarker improves the predictive utility of poor outcome. A combination of DAS score with IMAR leads to an AUROC of 0.91 ((±0.04) with 95% confidence intervals of 0.81-0.99, and a sensitivity of 74% and specificity of 92%. This provides an excellent predictive utility to assess mortality risk. (FIG. 9), whilst also reflecting worsening organ failure and inflammation, elements of the pathophysiology of liver failure, that may be targeted by specific interventions such as albumin dialysis and therapies to reduce inflammation. Methods of the invention such as DASIMAR could thus potentially also be used to monitor response to intervention.

Accordingly, methylarginines (such as DAS) and IMAR are suggestive of markers for disease progression and may be used in combination. The invention thus relates to a method for assessing the likelihood of progressive liver dysfunction and the development of multi-organ failure.

The assessment of liver function may be useful in a wide range of situations. For example, the method allows the patients with liver dysfunction to be distinguished from those with no liver dysfunction. Thus, the progression of liver disease may be monitored using the method of the invention; in particular those patients who are likely to suffer from a deleterious outcome may be identified. That is to say, the method of the invention may be used to predict the outcome of liver disease.

The method of the invention may also be used inter alia to assess liver function in post-liver transplantation, to assess liver function in reperfusion injury in a graft post-liver transplantation or assessing liver function in patients who develop multi-organ failure and sepsis.

Liver failure is the final stage of liver disease. Liver failure is divided into types depending on the rapidity of onset. Acute liver failure develops rapidly, but chronic liver failure may take months or years to develop. By definition, liver failure occurs when the liver is so diseased, and functioning so poorly, that encephalopathy is evident. Any progressive liver disease can result in liver failure; examples include: acetaminophen toxicity, cirrhosis, viral hepatitis, and metastatic cancer of the liver. Other signs of liver disease such as jaundice, ascites, fetor hepaticus, and failure of coagulation indicate that the liver is having trouble performing its normal physiological duties, but it is not termed liver failure until the mental status changes appear.

The prognosis for patients with liver disease is difficult to estimate because the condition has many causes. According to the invention, it is, however, possible to predict the clinical outcome of liver disease, in particular in patients with acute liver failure, as well as in those with ACLF. It may also be possible to identify early evolution of organ failure. In addition, those patients with progressive liver failure in whom early intervention is justified may be identified. Changes involved in liver transplants may also be identified using the method of the invention.

Accordingly, the method of the invention may be carried out on an individual whose liver is decompensated or who shows features of hepatic encephalopathy. The individual's liver may be in the compensated state. The individual may have chronic liver disease. The individual may have liver cirrhosis, for example with or without alcoholic hepatitis. The individual may have chronic liver failure, acute-on-chronic liver failure or acute liver failure. The individual may have hepatic encephalopathy.

The onset of both acute and chronic liver disease may be due to a xenobiotic cause. For example, the individual may have been exposed to a chemical, drug or some other agent which causes liver damage. The individual may have a reaction to an over-the-counter, prescriptive or "recreational" drug which causes liver damage. The individual may have been taking Rezulin™ (troglitazone; Parke-Davis), Serzone™ (nefazodone; Bristol-Myers Squibb) or other drugs thought to cause liver damage. The individual may be one who has had an overdose of a particular drug or exceeded the recommended dosage of a drug capable of causing liver damage. For example, the individual may have taken an overdose of paracetamol. The individual may have been exposed to chemicals which can cause liver damage such as, for example, at their place of work. For example, the individual may have been exposed to such chemicals in an industrial or agricultural context. The individual may have consumed plants which contain compounds which can cause liver damage, in particular this may be the case where the individual is an animal, such as a herbivore. For example, the individual may have consumed a plant containing pyrolizidine alkaloid such as ragwort. The individual may have been exposed to environmental toxins thought to cause liver disease.

Drug-related liver toxicity comprises more than 50% of all cases with acute liver disease (acute liver failure). Acetaminophen-(also known as paracetamol and N-acetyl-p-aminophenol) toxicity is the most common cause of acute liver failure in the United States and Great Britain. Long-term moderate to heavy alcohol users who tale acetaminophen in therapeutic or modestly excessive doses are at risk of severe hepatic injury and possibly acute liver failure. Alcohol use potentiates the toxic effects of acetaminophen. Idiosyncratic drug toxicity also contributes to acute liver failure. Idiosyncratic drug toxicity is thought to be a hypersensitivity response wherein the individual responds to a drug in a pharmacologically abnormal way. This abnormal response can lead to acute liver failure.

The acute liver failure or chronic liver disease may be caused by infection with a pathogenic organism. For example, the liver disease may be due to viral infection. In particular, the individual may be infected, or have been infected, with a virus which causes hepatitis. The individual may have chronic viral hepatitis. The virus may, for example, be hepatitis B, C or D virus. In some cases, and in particular where the individual has viral hepatitis, the individual may also be infected with HIV-I or II. The individual may have AIDS. It is possible that the individual may have been, or be, infected with other organisms which cause liver disease and in particular those which are present in the liver during some stage of their life cycle. For example, the individual may have, or have had, liver fluke.

The individual may have an inherited disease which causes, or increases the risk of, chronic liver disease. For example, the individual may have one or more of hepatic hemochromatosis, Wilson's disease or $\alpha$-1-antitrypsin deficiency. The individual may have an inherited disorder which causes some kind of structural or functional abnormality in the liver which increases the likelihood of liver fibrosis. The individual may be genetically predisposed to develop an autoimmune disorder which damages the liver and hence which can contribute to liver fibrosis.

The chronic liver disease may be alcohol-induced. A man or woman to be treated may be, or have been, an alcoholic. He or she may be, or have been, consuming on average 50 or more units of alcohol per week, 60 or more units of alcohol per week, 75 or more units of alcohol per week and even 100 or more units of alcohol per week. The man or woman may be, or have been, consuming on average up to 100 units of alcohol per week, up to 150 units of alcohol per week and even up to 200 units of alcohol per week. The measurement of one unit of alcohol differs from country to country. Here, one unit equals 8 grams of ethanol in accordance with the United Kingdom standard.

The man or woman may have been consuming such levels of alcohol for 5 or more years, 10 or more years, 15 or more years or 20 or more years. The individual may have been consuming such levels of alcohol for up to 10 years, up to 20 years, up to 30 years and even up to 40 years. In cases of alcohol-induced liver cirrhosis the individual may be aged, for example, 25 years or over, 35 years or over, 45 years or over and even over 60 years.

The individual may be male or female. Women may be more susceptible to the adverse effects of alcohol than men. Women can develop alcoholic chronic liver disease in a shorter time frame and from smaller amounts of alcohol than men. There seems to be no single factor to account for increased susceptibility to alcoholic liver damage in females, but the effect of hormones on the metabolism of alcohol may play an important role.

Thus, the individual may be suffering from alcoholic hepatitis. Alcoholic hepatitis may range from a mild hepatitis, with abnormal laboratory tests being the only indication of disease, to severe liver dysfunction with complications such as jaundice (yellow skin caused by bilirubin retention), hepatic encephalopathy, ascites, bleeding esophageal varices, abnormal blood clotting and coma.

In the invention, the individual may have one or more of a number of other conditions known to result in liver damage such as, for example, primary biliary cirrhosis, autoimmune chronic active hepatitis, and/or schistosomiasis (parasitic infection). The individual may have or have had a bile duct blockage. In some cases, the underlying cause of liver disease may not be known. For example the individual may have been diagnosed as having cryptogenic cirrhosis. Accordingly, the individual may be suspected of having any of the conditions listed herein.

Methods for diagnosing liver disease such as acute liver failure and hepatic encephalopathy are well known in the art and in particular to clinicians and veterinarians in the field. Preferably, the individual will have been diagnosed as having a liver disease and hepatic encephalopathy, for example by a medical or veterinarian professional. The individual may display one or more symptoms associated with liver disease such as one or more of jaundice, ascites, skin changes, fluid retention, nail changes, easy bruising, nose bleeds, oesophageal varices, and in male individuals may have enlargement of breasts. The individual may display exhaustion, fatigue, loss of appetite, nausea, weakness and/or weight loss. The individual may also display one or more symptoms associated with hepatic encephalopathy such as one or more of confusion, disorientation, dementia, stupor, coma, cerebral edema, multiorgan failure (respiratory failure, cardiovascular failure or kidney failure), muscle stiffness/rigidity, seizures or speech impairment. The individual to be treated may or may not be taking other drugs to treat liver disease. The individual to be treated may be at risk of developing hepatic encephalopathy.

The liver disease may have been, or be, confirmed by physical examination including techniques such as ultrasound. Liver biopsies may have been taken to look for build up of fibrosis, necrotic cells, cellular degeneration and/or inflammation and other characteristic features of liver disease. Liver function may have been assessed in the individual to determine whether this is compromised in the individual. The nature and underlying cause of the liver disease may be characterized. Any history of exposure to causative agents of liver disease may be determined.

The individual to be treated may be at risk for hepatic encephalopathic episodes, for example patients who are awaiting liver transplants, surgical and/or portal hypertension patients. A person at risk for hepatic encephalopathic episodes is a person who has not suffered any hepatic encephalopathic episodes or has not suffered any hepatic encephalopathic episode for an extended period of time (about 12 weeks or longer), but has a disorder or medical condition which creates a risk of hepatic encephalopathic episodes. A hepatic encephalopathic episode is a clinical condition characterised by the presence of cerebral dysfunction in patients with liver disease or dysfunction. There is a wide spectrum of mental disturbances in hepatic encephalopathy which range from minimal where the main effects are a reduction in the quality of life, to overt which leads to coma and ultimately death.

The method of the invention may be applied to monitoring liver dysfunction, i.e. as a test of liver function, in the context of, for example, (i) post-liver transplantation—the inventors have shown that after acute liver failure patients have been transplanted, there is a progressive reduction in ADMA and a slower drop in SDMA reflected in a lower DAS score; (ii) reperfusion injury in a graft after liver transplantation; (iii)

critically ill patients in ITU who develop multi-organ failure-liver dysfunction may be a primary driver and, therefore, the method of the invention can identify this early on and track progress of this i.e. may predict those likely to get further organ failure (for example, 1, 2 or 3 organs) and die. Accordingly, the individual on which the method of the invention is practiced may be a liver transplant patient, an individual suffering from reperfusion injury, for example in a graft after liver transplantation or a patient at risk of developing or who has developed multi-organ failure.

In the invention, the level of methylarginine(s) and IMAR is determined in an individual.

Typically the method is carried out in vitro on a sample from the individual. The sample will generally be from a tissue known to contain methylarginine(s) and IMA and albumin. The sample typically comprises a body fluid of the individual and may, therefore, be serum for example. Alternatively, or additionally, the sample may comprise urine, cerebrospinal fluid or hepatic tissue. Such samples may be obtained in any appropriate way. Methods for obtaining serum and hepatic tissue are well known to those skilled in the art.

Levels of methylarginine(s) in an individual, in particular ADMA and SDMA, may be measured in any convenient fashion. Such methods are well known to those skilled in the art. For example, the level of methylarginine(s) in a sample may be measured using fragmentation specific stable isotope dilution electrospray tandem mass spectrometry, or by ion-exchange extraction followed by HPLC with fluorescence detection. Further detection techniques include capillary electrophoresis.

IMAR may be also be determined using any convenient method known to those skilled in the art. For example, the Abbott Aeroset Bomocresol Purple (BCP) test may be used for the measurement of serum albumin. The concentration of IMA may then be determined by the addition of a known amount of Co(II) to a serum specimen and measurement of the unbound Co(II) by a colorimetric assay using dithiothreitol.

The level of methylarginines individually or in combination, (for example ADMA+SDMA=DAS score), and IMAR may be used to predict the clinical outcome of liver disease in the individual.

Preferably, the method used for determining the level of methylarginine(s) (such as ADMA and SDMA) and IMAR will be one which it is possible to carry out relatively quickly and cheaply. The method used may be one which it is possible to carry out at the bedside so as to simplify measurement within a clinical setting. For example, an assay kit such as an ELISA may be used to measure the level of methylarginines or to determine IMAR.

A DAS score is calculated from the summation of measured values of the 2 methylated arginines in plasma (asymmetric dimethylarginine [ADMA] and its' stereo-isomer symmetric dimethylarginine [SDMA]). These two variables reflect both inflammatory status and identify early evolution of organ failure. Patients that die have a significant percentage increase in DAS compared with survivors, in whom there is a relative reduction.

Accordingly, in the method of the invention an elevated DAS score (or a score generated from one or other of the components thereof), as compared with the equivalent score in a patient not suffering from liver disease or a survivor of liver disease, is a reliable predictor of the progression to organ failure or, more critically, deleterious outcome, i.e. mortality.

An elevated DAS score (or a score generated from one or other of the components thereof) thus acts as a reliable predictor of outcome in patients with acute liver failure, including changes with liver transplantation, as well as in those with ACLF.

It is believed that application of this elevated score (as compared with non-liver disease individuals or liver disease survivors) helps define those patients with progressive liver failure in whom early intervention with liver support systems is warranted. Also, such elevated scores may be used to select individuals from a population of candidates who are to receive liver transplants.

Patients with alcoholic liver disease who die have a significantly increased IMA:albumin ratio as compared with survivors. Furthermore, as with the DAS value, IMAR appears to reflect inflammatory status and there-by the underlying pathological evolution of the disease. Accordingly, IMAR may be a useful predictive test of liver disease progression, and, in particular, mortality in these patients.

A combination of a dimethylarginine Score (DAS) with IMAR as a combined biomarker, improves the predictive utility of poor outcome, with an AUROC of 0.91 ((±0.04) with 95% confidence intervals of 0.81-0.99, and a sensitivity of 74% and specificity of 92%. This provides an excellent predictive utility to assess mortality risk, whilst also reflecting worsening organ failure and inflammation, elements of the pathophysiology of liver failure, that may be targeted by specific interventions such as albumin dialysis and therapies to reduce inflammation.

Accordingly, in the method of the invention, an elevated level of methylarginine(s), as compared with the level of methylarginine(s) in an individual not suffering from liver disease or in an individual who is a survivor of liver disease, is indicative of a progression of liver disease, impaired hepatic function, increased risk of mortality in the individual.

An increase in the combined level of ADMA and SDMA, as compared with the combined level of ADMA and SDMA in an individual not suffering from liver disease or in an individual who is a survivor of liver disease, is indicative of a progression of liver disease, impaired hepatic function, increased risk of mortality in the individual.

An increase in IMAR, as compared with IMAR in an individual not suffering from liver disease or in an individual who is a survivor of liver disease, is also indicative of a progression of liver disease, impaired hepatic function, increased risk of mortality in the individual.

In the methods described above, an increase in the level of methylarginine(s), such as an increase in the combined level of ADMA and SDMA, and an increase in IMAR, as compared to an individual not suffering from liver disease or in an individual who is a survivor of liver disease, is indicative of a progression of liver disease, impaired hepatic function, increased risk of mortality in the individual.

Ideally, a DAS score (or a component score thereof) or a DASIMAR score should be predictive of a specific outcome such as mortality, i.e. ideally the skilled person would like to be able to determine clinical outcome, for example survival or death, on the basis of such scores.

A receiver operating characteristic (ROC) curve may allow this to be achieved. Such curves explore the relationship between the sensitivity and specificity of a clinical test, such as DAS or DASIMAR, for a variety of different cut points, thus allowing the determination of an optimal cut point, i.e. it will be desirable to select a cut point above which, deleterious outcome of liver disease is indicated and below which survival is indicated.

Commonly used measures of the performance of a clinical test are the sensitivity and specificity. Sensitivity is the probability that the disease (or outcome in the case of the present invention) is diagnosed when it is actually present and specificity is the probability that the disease is identified as being absent when it properly is absent. Ideally, both of sensitivity and specificity should be one. However, changing the cut point to try to increase one of sensitivity and specificity will usually result in a decrease in the other.

The ROC curve is a graphical technique for establishing the optimal cut point.

In order to construct a ROC curve one needs to calculate the sensitivity and specificity for each possible cut point value. To make the ROC graph, the X-axis is 1 minus the specificity and the Y-axis is the sensitivity. A diagonal line is drawn from the lower left corner to the upper right corner. This graph reflects the characteristics of a test with no discriminating power. The closer the graph gets to the upper left corner the better it is at discriminating between cases and non-cases. An index of the goodness of the test is the area under the curve—the closer this value is to one the better the discriminating power of the test.

Accordingly, an ROC curve may be used to establish a cut point for a DAS score (or component score thereof) or a DASIMAR score. A score above the cut point may be indicative of deleterious outcome such as mortality, whereas a score below the cut point may be indicate of non-deleterious outcome such as survival.

The cut point can be selected depending on the requirements of the test, for example whether it is more important to exclude false positives or whether it is more important to identify all true positives. In the case of a test for identifying those patients admitted with liver failure who will die, it is important that all of those patients are identified in which case the cut point may well also identify a number of false positives.

In the method of the invention, a cut point may indicate a particular outcome of liver disease, such as survival, or be indicative of progression of liver disease, for example onset of acute liver disease.

An appropriate cut point may be identified by those skilled in the art. For example, a DAS cut point of 1.52 has been shown to be a useful predictor when evaluating survival in patients suffering from alcoholic cirrhosis with alcoholic hepatitis.

The method of the invention may be carried out in combination with one or more additional scoring systems used to assess the severity of liver disease and hepatic encephalopathy and also the prognosis of subjects. For example, from about two, three, four or more to about five, six, seven, eight or more scoring systems may be combined with those of the invention. Such additional scoring systems include the Child-Pugh, West Haven Criteria, Glasgow Coma Scale or modified Child-Pugh scoring system. Alternatively, or in addition, DF, sequential organ failure assessment (SOFA), MELD or Acute Physiology and Chronic Health Evaluation II (APACHE II) may be used scoring system may be used. Points are assigned to parameters including serum bilirubin levels, serum albumin levels and to signs including presence of ascites or encephalopathy. Subjects to be treated may be classified in Child-Pugh class A, B or C. Generally subjects to be treated are classified in Child-Pugh class C.

The invention also provides a test kit suitable for predicting the outcome of liver disease in an individual, which test kit comprises means for determining the level of one or more methylarginines and IMAR in the individual.

A test kit of the invention may also comprise an agent useful in the treatment of liver disease.

A test kit of the invention may optionally comprise, appropriate buffer(s), enzymes, for example a thermostable polymerase such as Taq polymerase and/or control polynucleotides. A kit of the invention may also comprise appropriate packaging and instructions for use in a method for predicting the outcome of liver disease in an individual.

The invention allows the identification of an individual who has increased risk of mortality. It may also allow the progression of liver disease to be monitored of the effects of intervention to be determined, i.e. the efficacy of treatment of liver disease in an individual may be monitored. Thus, the method may be carried out a number of times in respect of the same individual and treatment to evaluate the effectiveness of a course of treatment for liver disease.

Individuals identified as being at an increased risk of mortality may then be treated accordingly.

The invention thus provides a method of treatment of liver disease, which method comprises determining whether or not the individual has an increased risk of mortality using the method as described above and then administering to the individual a therapeutically effective amount of an agent useful in the treatment of liver disease.

The invention also provides use of an agent which is useful in the treatment of liver disease for use in, or for use in the manufacture of a medicament for use in, a method of treatment of liver disease in an individual, wherein the individual has been identified as suffering from an increased risk of mortality using the method set out above.

Thus, the condition of an individual identified as having an increased risk of mortality may be improved by administration of an agent which is used in the treatment of liver disease. A therapeutically effective amount of an agent which is used in the treatment of liver disease may be given to an individual identified according to a method of the invention.

Even when an individual is identified as having an increased risk of mortality, the progression to complete liver failure may be irreversible. In this case, steps may be taken to slow down the decline of liver function. The patient's diet may be restricted. Protein consumption will typically be kept at optimal levels: if it is too high, it can cause brain dysfunction, but too little can cause weight loss. Alcohol must be completely avoided and sodium consumption may be kept down to help to prevent ascites, the accumulation of fluid in the abdomen. Liver dialysis may be appropriate. Liver transplantation is the definitive treatment for liver failure, but is not an option for all patients and the supply of livers is limited. Accordingly, the method of the invention may be used to stratify potential recipients of liver transplants; those most risk of death may be identified. Medications, such as lactulose may be given to relieve the symptoms of liver failure.

An agent which is used in the treatment of liver disease may be administered in a variety of dosage forms. Thus, an agent may be administered orally, for example as tablets, troches, lozenges, aqueous or oily suspensions, dispersible powders or granules. The agent which is used to treat disease may also be administered parenterally, either subcutaneously, intravenously, intramuscularly, intrasternally, transdermally or by infusion techniques. The agent may also be administered in the form of a suppository. A physician will be able to determine the required route of administration for each particular patient.

The formulation of an agent used in the treatment of liver disease will depend upon factors such as the nature of the exact agent, whether a pharmaceutical or veterinary use is intended, etc. An agent which is to be used to treat liver disease may be formulated for simultaneous, separate or sequential use.

An agent used in the treatment of liver disease is typically formulated for administration in the present invention with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

A therapeutically effective amount of an agent used in the treatment of liver disease may be administered to a patient identified as having liver disease using the method of the invention. The dose of an agent which used in the treatment of liver disease may be determined according to various parameters, especially according to the substance used; the age, weight and condition of the patient to be treated; the route of administration; and the required regimen.

Again, a physician will be able to determine the required route of administration and dosage for any particular patient. A typical daily dose is from about 0.1 to 50 mg per kg of body weight, according to the activity of the specific inhibitor, the age, weight and conditions of the individual to be treated, the type and severity of the degeneration and the frequency and route of administration. Preferably, daily dosage levels are from 5 mg to 2 g.

A suitable agent may be used in the manufacture of a medicament for use in a method of treatment of liver disease in an individual, wherein the individual has been identified as suffering from liver disease according to the method of the invention as described above.

Thus, a method for the treatment of liver disease in an individual may comprise: (i) determining whether the individual is at risk of mortality using a method of the invention as described above; and (ii) administering to an individual identified in (i) as at risk of mortality, a therapeutically effective amount of an agent as disclosed above.

Products containing means for predicting the outcome of liver disease in an individual and an agent which may used in the treatment of liver as a combined preparation for simultaneous, separate or sequential use in a method of treatment of the human or animal body by therapy. Thus, such products may comprise both means for diagnosis and means for therapy.

All publications and patent applications mentioned in this specification are indicative of the level of those skilled in the art to which this invention pertains.

All publications and patent applications are herein incorporated by reference to the same extent as if each individual publication or patent application was specifically and individually to be incorporated by reference.

Although the foregoing invention has been described in some detail by way of illustration and example for purposes of understanding, it will be clear to those skilled in the art that certain changes and modifications may be practiced within the scope of the appended claims.

The following Examples illustrate the invention:

EXAMPLES

Example 1

Increasing Dimethylarginine Levels are Associated with Adverse Clinical Outcome in Severe Alcoholic Hepatitis Methods Study Design All patients or their relatives gave written informed consent or assent, respectively, in accordance with the Declaration of Helsinki of the World Medical Association, 1989, and the study was approved by the local ethics committee. Patients were included with evidence of an acute decompensation of alcoholic liver disease (increasing ascites, pedal oedema or progressive jaundice) with clinical and radiological evidence of cirrhosis, and with a current history of alcohol abuse (alcohol consumption of >80 g alcohol/day for men and >60 g/day for women up until the time of admission). Patients were excluded if they were <18 or >75 years and had evidence of: additional or another aetiology of liver disease; severe cardiac dysfunction or renal failure (creatinine>150 μmol/L); hepatic/extra-hepatic malignancy; hepatic encephalopathy≧Grade 2 (precluding informed consent), and if there was microbiological evidence (culture of urine, blood, sputum and ascites) indicative of infection after 72 hours of broad-spectrum antibiotic therapy.

Patients were studied at the time of transjugular liver biopsy (within days 1-3 of admission), performed to assess the severity of liver dysfunction in those with ascites or/and coagulopathy. Patients were classified as having alcoholic hepatitis superimposed on cirrhosis (AH+C+) on subsequent histological examination. The histological criteria used to define AH+C+ included the presence of: hepatocyte balloon degeneration; Mallory bodies; neutrophil infiltration and apoptotic acidophilic bodies.[18] All patients received supportive therapy including, nutrition: 2000 kCal/day with 72 g protein/day; vitamin supplementation: 1 multivitamin capsule and 200 mg Thiamine per day after initial parenteral B vitamin supplementation (intra-venous Pabrinex three times daily for 2 days). Local protocol driven treatment was initiated for the development of complications including, sepsis (antimicrobials after culture); hepatorenal syndrome (terlipressin 0.5-2 mg intravenously up to six times daily in conjunction with 60 g of salt poor albumin [20 g/100 ml]); organ failure (full intensive care support including haemofiltration or/and ventilation, as indicated). Given the on-going debate on the use of corticosteroids and anti-TNF antibody treatments in the UK for acute alcoholic hepatitis, no patients received these therapies during the study.

Measurements: Hemodynamic studies were performed following an overnight fast and a one hour supine resting period. Patients were sedated for the procedure using Midazolam (mean dose of 4 mg; Phoenix Pharma Ltd., Gloucester, UK), and heart rate and non-invasive mean arterial blood pressure monitoring was conducted throughout. A Systemic Inflammatory Response Syndrome (SIRS) score for each patient[19] was established using the criteria: temperature>38° C.; a heart rate>90 beats/minute; tachypnea>20 breaths/minute; white blood cell count of >12×10$^9$/L or <4×10$^9$/L or the presence of more than 10% immature neutrophils, Hepatic venous pressure gradient (HVPG): A 5Fr Berenstein occlusion balloon catheter (Boston Scientific, Cork, Ireland) was introduced via the right internal jugular route into the right hepatic vein under fluoroscopic screening (Toshiba Spot Film Device Model: SA-900U; Tochigi-ken, Japan). Wedged and free hepatic venous pressure measurements, performed in triplicate, were recorded via pressure transducer sets (Medex Medical, Rossendale, Lancashire, UK) on a Hewlett Packard monitor (Model 86S, HP, USA). HVPG was calculated as the difference between wedged and free hepatic venous pressure.

Sampling and Assays: Blood was collected from an artery and hepatic vein in pre-cooled heparinized/EDTA coated tubes (Becton Dickenson, Drogheda, Ireland). Routine hematology, liver biochemistry and C-reactive protein were measured in all patients. Plasma creatinine was assessed by mass spectrometry given the difficulties with accuracy of the Jaffe assay in cholestatic states.[20] Additional plasma samples were separated by centrifugation and plasma stored at −80° C. for subsequent analysis of cytokines, chemokines and ADMA. Hepatic tissue acquired was either formalin fixed or snap-frozen in liquid nitrogen and stored at −80° C. for subsequent assessment of tissue ADMA concentration and for protein estimation of PRMT 1 and DDAH II. Blood samples drawn from a "control" group of 12 healthy volunteers (9 male), with no history of alcohol excess and no known past medical history, were used to evaluate "normal" ranges for ADMA and SDMA.

Cytokines/chemokines: TNFα, interleukin-6 (IL-6), interleukin-8 (IL-8) and soluble TNF receptors I and II (TNF-RI, TNF-RII) were measured using standard commercial assay kits (BioSource, Nivelles, Belgium) as described previously.[21] The lower limit of detection was estimated to be 5 pg/ml and the intra-assay coefficient of variation was 4.5-5.5%.

ADMA: Plasma ADMA was measured using fragmentation specific stable isotope dilution electrospray tandem mass spectrometry. Samples (50 µl) were de-proteinized with acetonitrile containing $^2$H$_6$-ADMA, chromatographed (acetonitrile:water, 1:1, with 0.025% formic acid) on a Teicoplanin guard column 10 mm×2.1 mm ID (Chirobiotic T, ASTEC Ltd, Congleton, UK), and analysed using a SCIEX API4000 (Applied Biosystems, Warrington, UK) in positive ion multiple reaction monitoring mode. The acquisition time was 2.5 min with an inject-to-inject time of <3 min. Within assay imprecision for ADMA was 2.1% at a concentration of 0.37 µmol/l. Inter assay imprecision for ADMA was 7.4%, 5.8%, and 5.1% at concentrations of 0.39, 1.15, and 3.96 µmol/l, respectively.

Tissue homogenates were prepared from snap frozen liver tissue in ice-cold HEPES buffer (20 mM, pH 7.4) containing EDTA (1 mM); sucrose (250 mM); valine (60 mM); protease inhibitor cocktail (at 1 ml/20 g tissue, containing: 4-(2-aminoethyl)benzenesulfonyl fluoride (AEBSF), pepstatinA, E-64, bestatin, leupeptin, and aprotinin; Sigma-Aldrich Co, UK); and PMSF (3.4 mg/ml). This was centrifuged (1000 g, 10 min, 4° C.) and the supernatant retained and measured for protein content using the Biurret method.[22] The supernatants from these preparations were extracted and assayed for ADMA using the method outlined above, but using 10 µl of each homogenate sample. Tissue ADMA concentrations were expressed as micromoles per milligram of protein.

DDAH and PRMT Western blot analysis: Biopsy specimens from the last 8 patients (4 with proven AH+C+ and 4 with alcoholic cirrhosis alone) were assessed for quantification of DDAH and PRMT. Homogenised frozen liver tissue was re-suspended in 100 µL of lysis buffer (PBS, pH 6.6, containing 0.1% SDS, 0.5% sodium deoxycholate and 1% Nonidet). After protein concentration determination, 30 ug of protein was separated by SDS polyacrylamide gel (12%) and transferred to a nitrocellulose membrane, which was blocked with 5% non-fat dry milk in PBS containing 0.1% Tween for one hour. Samples were incubated overnight at 4° C. with the primary antibody (anti mouse monoclonal DDAH II antibody, raised against amino acids 241-255- a sequence unique to human DDAH II; or anti rabbit polyclonal PRMT-1 antibody [Abcam plc, UK], 1:1000), before washing and further incubation with anti-mouse or anti-rabbit horseradish peroxidase-conjugated secondary antibody (DDAH II and PRMT-1, respectively) at a dilution of 1:3000. The membranes were developed with enhanced chemiluminescence substrate plus (ECL plus, Amersham, UK). Blots were imaged and quantified using Genesnap/Gene tools (Syngene, SLS, UK). Membranes were then stripped at 55° C. and re-probed using an α-tubulin mouse anti-human monoclonal primary antibody (Sigma-Aldrich, UK) followed by secondary anti-mouse antibody and developed as above, in order to quantify the expression of PRMT and DDAH by correcting it for the α-tubulin content.

Statistical Analysis: Data are shown as median [range] or mean±standard error of the mean (SEM). Two-tailed unpaired t-tests were used to define differences between means of normally distributed data of equal variance, using a commercially available package (Graph Pad Prism, version 4.0; Graph Pad Software, Inc., San Diego, Calif., USA). For statistical evaluation of data that was not normally distributed, a Mann-Whitney test (Graph Pad Prism) was used. Results were considered significant if $P<0.05$. Comparison between multiple groups was by analysis of variance (ANOVA) with a Bonferroni correction for multiple comparisons. Calculation of correlations between variables was performed using regression analysis software; Excel 2003 (Microsoft Corporation, WA).

Results

Patients: From a total number of 64 patients assessed over a fifteen month period, 52 patients were included in the study, with a mean Pugh score[23] for the group of 10±0.3 reflecting de-compensated cirrhosis in this cohort. This elevated index of severity was complemented by a raised MELD score[24] and the elevated mean hepatic venous pressure gradient (HVPG) of 19±1 mmHg for the whole group, reflecting advanced portal hypertension. 12 patients were excluded: 7 with concomitant viral hepatitis, 3 with severe renal dysfunction, 1 patient with no histological evidence of cirrhosis, and 1 patient with overwhelming sepsis. Using the standard histological criteria defined above[18] the 52 patients included in the study were then divided into those with cirrhosis and inflammation as alcoholic hepatitis [AH+C+] (n=27), and those with alcoholic cirrhosis alone [AH−C+] (n=25), as described in the patient characteristics table-1. Grading of severity of necroinflammation in AH+C+ biopsies was by application of a scoring system similar to that suggested for non-alcoholic steatohepatitis,[25] and all included patients had a moderate-severe grading agreed upon by 2 independent histopathologists.

In addition to histological criteria, all AH+C+ patients had acute severe AH as evidenced by a mean Maddrey discriminant function (DF) score of 46±6,[26] and reflected in the significantly elevated plasma bilirubin levels and prothrombin times compared to the AH−C+ patients, as summarized in Table 1. The serum aminotransferases were not statistically different between the groups (P=0.46). Mean serum creatinine levels were within normal laboratory reference range for both groups, although the mean creatinine value was higher in AH+C+ patients compared to AH−C+, P=0.01. Twenty of the twenty-seven AH+C+ patients had moderate to severe ascites compared with ten of tle twenty-five AH−C+ patients; P=0.008. Twelve AH+C+ patients had ≧grade 2 hepatic encephalopathy compared to four out of twenty-five AH−C+ patients; P=0.02.

Inflammatory Markers: AH+C+ patients had significantly elevated inflammatory indices compared with AH−C+ patients as evidenced by higher plasma CRP (P<0.001), elevated white blood cell count (P<0.001), and Systemic Inflammatory Response Syndrome (SIRS) scores (P<0.001). Further evidence of on-going inflammation in the AH+C+ patients was evident from significantly greater plasma TNFα (P<0.01), TNF-R1 (P<0.01) and TNF-R2 (P<0.001) levels, and elevated IL-6 (P<0.01) levels in AH+C+, compared with AH−C+ patients.

HVPG: AH+C+ patients had significantly higher mean HVPG compared to AH−C+ patients (22±1.9 vs. 15.5±1.6 mmHg, P<0.01), reflecting more advanced portal hypertension.

Patient Outcome: There were thirteen in-patient deaths in the fifty-two studied patients, twelve with AH+C+ and one amongst those with only cirrhosis. Of the AH+C+ deaths, eight developed renal failure, four of whom also had concomitant sepsis and developed multi-organ failure. Two patients died from uncontrolled GI bleeding, whilst two other patients failed to recover from spontaneous bacterial peritonitis with gram negative organisms, with development of a coagulopathy and multi-organ failure. (Table 2). Amongst the fifteen AH+C+ patients that survived and were successfully discharged from hospital within 28 days, six had evidence of infection during their admission, one patient with renal failure responded to supportive therapy and two had an episode of controlled variceal bleeding. AH+C+ patients who died had no significant difference in discriminant function (P=0.3), Pugh score (P=0.2) or MELD (P=0.6) score compared with surviving AH+C+ patients.

In the cirrhotic only (AH−C+) group, one in-patient died from renal failure despite supportive therapy. Of the remaining 24 AH−C+ patients, who were successfully discharged from hospital, five had an episode of infection recorded during their admission, and there was 1 controlled variceal bleed. AH−C+ patients had significantly lower Pugh scores (P<0.001) and MELD scores (P<0.001) than AH+C+ survivors (n=15).

ADMA: The mean plasma ADMA levels were higher in the 52 patients compared to 12 healthy controls [age: 38 (31-55); 9 male]: 0.59±0.03 vs. 0.37±0.01 μmol/L; P<0.001. Furthermore, AH+C+ patients had significantly higher ADMA values compared to the AH−C+ group: 0.69±0.04 vs. 0.49±0.02 μmol/L; P<0.001, as illustrated in FIG. 1a. Hepatic tissue ADMA levels were also considerably higher in AH+C+ patients compared to AH−C+ (97±23 vs. 27±13 μmol/mg protein, P<0.05), and were shown to correlate with portal pressure, R=0.61, P<0.05. Plasma ADMA levels were significantly greater in those patients that died during their admission (n=13) compared with survivors. (n=39) (0.77±0.08 vs. 0.53±0.02 μmol/L; P<0.001); FIG. 1b. Further sub-analysis revealed significantly greater ADMA levels between discharged AH+C+ patients and the non-inflamed AH−C+ patients (0.62±0.04 vs. 0.49±0.02 μmol/L, P<0.01). Furthermore, levels of ADMA were higher in AH+C+ patients that died compared to AH+C+ survivors, P<0.05. FIG. 1c.

SDMA: The mean plasma SDMA level for the 52 patients although higher was not statistically significantly greater than in controls: 0.77±0.08 vs. 0.46±0.01 μmol/L, P=0.08. However, levels of SDMA were significantly higher in AH+C+ patients compared to AH−C+ (1.03±0.1 vs. 0.48±0.03 μmol/L; P<0.001). SDMA levels amongst AH−C+ patients were similar to healthy volunteers (P=0.67) [FIG. 2a]. Levels of SDMA were significantly higher in patients that died during admission compared with all survivors, (1.6±0.35 vs. 0.6±0.05 μmol/L; P<0.001) [FIG. 2b]. Further sub-analysis of AH+C+ patients demonstrated a significantly greater SDMA in those patients that died compared with survivors, in whom the mean SDMA was 0.8±0.1 μmol/L; P<0.05 [FIG. 2c]. There was also, however, a significant difference in SDMA between AH+C+ survivors and non-inflamed AH−C+ survivors in whom the mean SDMA level was 0.48±0.03; P<0.01.

Figure 3:
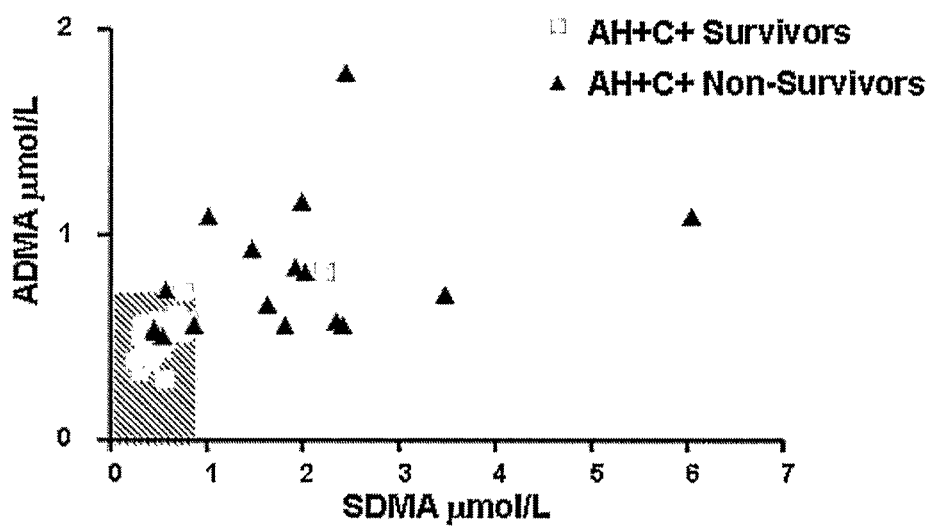
FIG. 3 shows ADMA compared with SDMA: A plot of ADMA vs. SDMA in AH+C+ patients demonstrates that at the cut-off value for SDMA of 0.9 μmol/L derived from receiver operator curves, number of deaths as predicted by ADMA using a cut-off 0.65 μmol/L, are not accounted for (denoted by the shaded area), suggesting a potential benefit of a combined score of ADMA+SDMA (DAS) to determine outcome.
Figure 5:
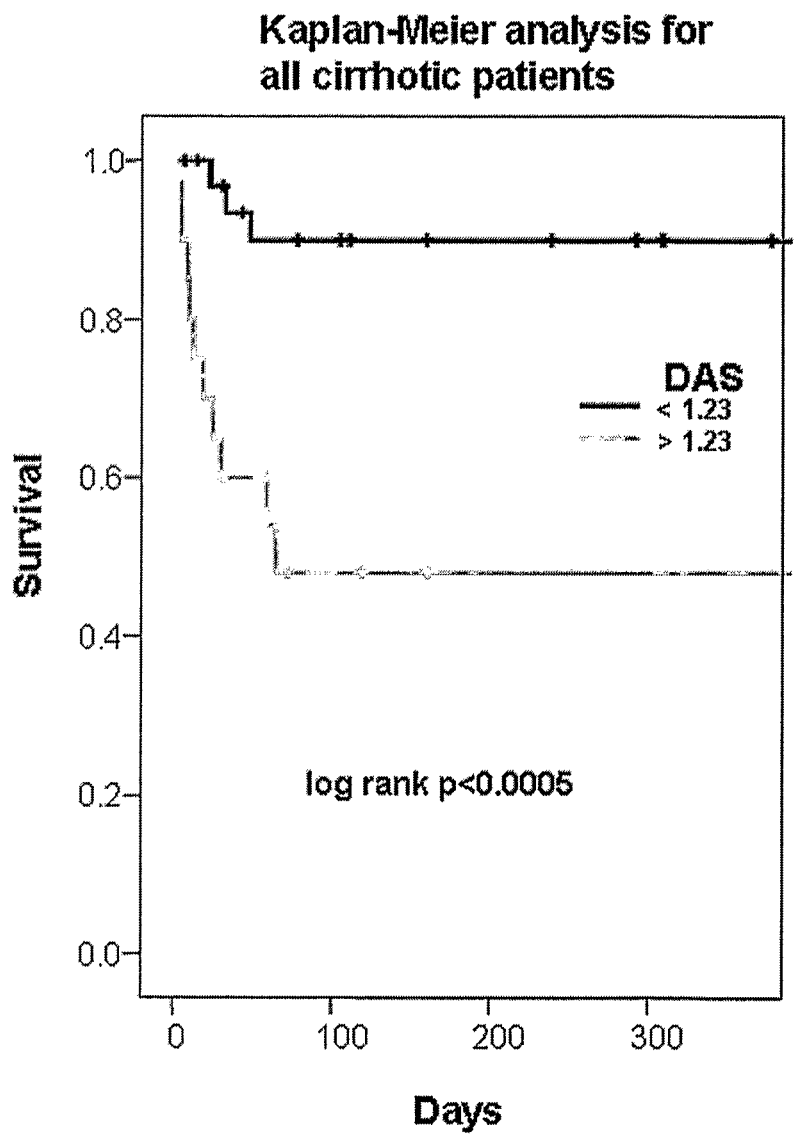
FIG. 5 shows Kaplan-Meier Survival curves of the admission dimethylarginine score (DAS): The figure shows a Kaplan-Meier survival analysis comparing in-hospital mortality in all studied alcoholic cirrhotic patients, based on admission DAS value <1.23 or >1.23 (P<0.0005). A higher DAS score significantly increases the risk of in-hospital mortality.
Figure 6:
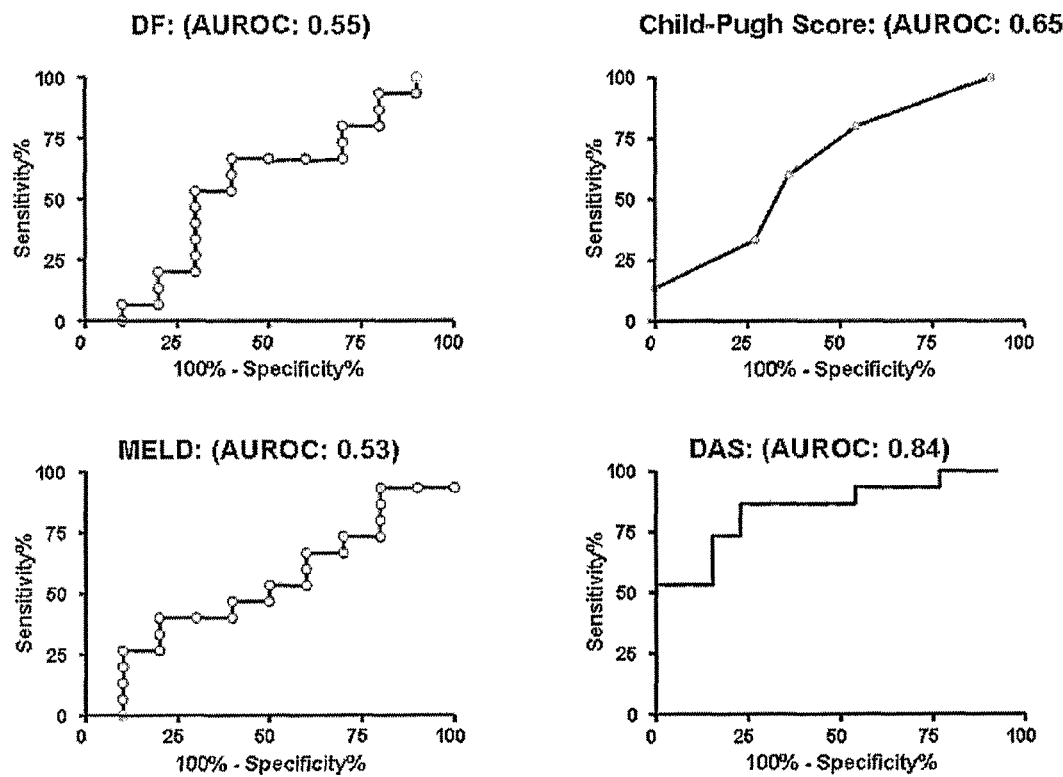
FIG. 6 shows receiver Operator Curves calculated for the prognostic scores-Discriminant Function (DF), Child-Pugh score, Model for End-stage Liver Disease (MELD) and the Dimethylarginine Score (DAS) in alcoholic hepatitis (AH+C+) patients: The ROC curves for DF, Child-Pugh, MELD and DAS are shown with the area under the curve (AUROC) listed. It is evident from these figures that in the subgroup of AH+C+ patients, the DAS value provides the most reliable predictor of mortality (AUROC=0.84), using a DAS cut-off of 1.52; this gives a sensitivity of 73% and a specificity of 83%.

Predictors of Survival: Baseline measurements (day 0-3) of ADMA and SDMA, together with the calculated MELD, Pugh Score and Discriminant Function at this time-point, were used to compare the predictive utility of these measures in determining in-patient survival, by the use of area under the curve (AUC) for receiver operator curves (ROC). The AUC for each of these predictive measures for all patients, and a separate analysis for AH+C+ patients, is listed in table 3. In addition, when ADMA was compared with SDMA in AH+C+ patients as shown in FIG. 3, the cut-off value for SDMA (<0.9) derived from its ROC, did not encompass all deaths as predicted by using an ADMA cut-off<0.65. We therefore, used a combined dimethylarginine score (DAS), calculated from the summation of ADMA and SDMA [DAS=ADMA+SDMA], to try and improve the predictive utility of an individual dimethylarginine level in determining survival. The calculated DAS was significantly higher in AH+C+ patients compared with AH−C+(1.9±0.2 vs. 0.96±0.04; P<0.001) Furthermore, the DAS value was significantly higher in non-surviving AH+C+ patients compared to survivors, 2.5±0.38 vs. 1.4±0.16; P<0.01. Indeed, the DAS value improved the specificity, whilst maintaining a high sensitivity of predicting outcome in all patients, and appeared at least as good in determining outcome as the Pugh score, DF or MELD, Table 3. Repeat dimethylarginine measurements from blood taken during admission in the 12 AH+C+ patients that died compared with 18 survivors (6 AH−C+) in whom repeat blood samples were available, revealed a significant percentage increase in DAS in those patents that died compared with survivors (P<0.01). FIG. 4. A Kaplan-Meier plot for all studied patients is shown in FIG. 5, and shows the significant decrease in-hospital survival in those patients with an admission DAS value>1.23, with a log rank of P<0.001. Furthermore, a DAS cut-off of 1.52 appeared to be a more useful predictor than all other scoring systems when evaluating survival in AH+C+ patients, as shown in FIG. 6.

Figure 7:
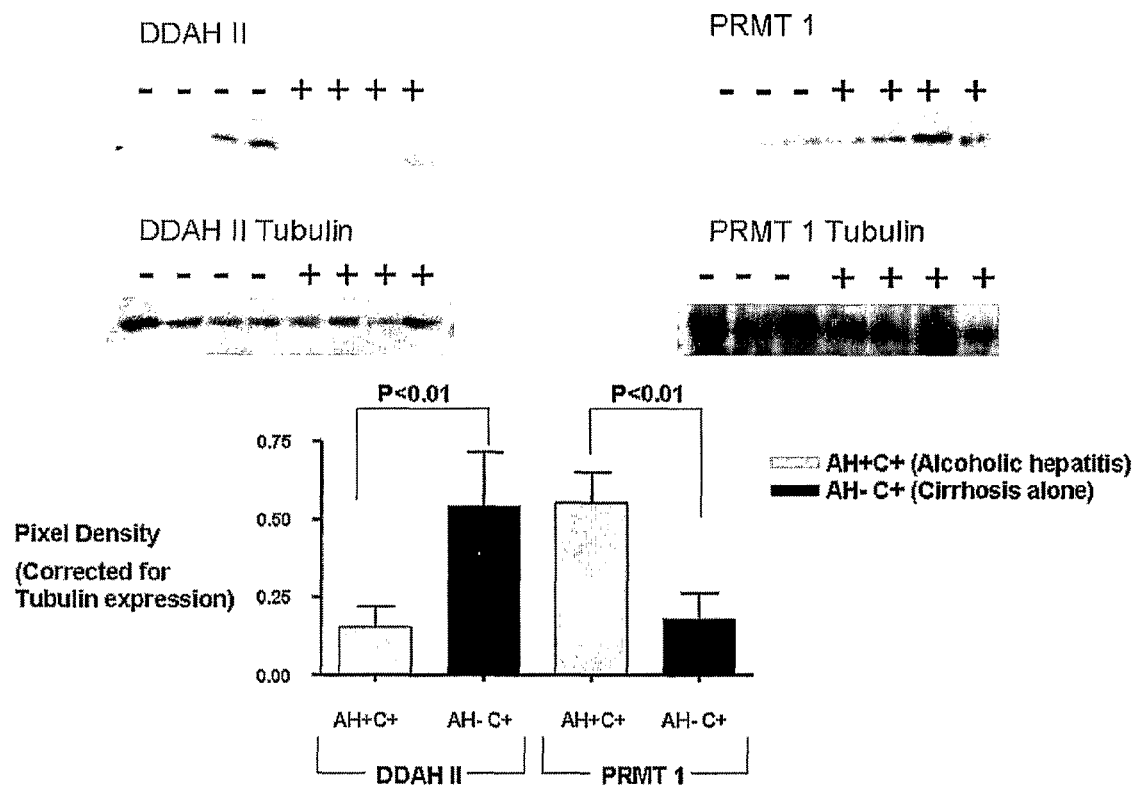
FIG. 7 shows DDAH II and PRMT-1 Protein Expression: Representative Western blots are shown for dimethylarginine-dimethylaminohydrolase-II (DDAH-II) and protein-arginine-methyltransferase-1 (PRMT-1) expression in the studied AH+C+ and AH−C+ patients, together with their corresponding α-Tubulin protein blots, to control for gel loading. A quantification of DDAH II and PRMT-1 densities on Western blots of all assessed patient biopsies is represented in the column bars for AH+C+ and AH−C+ patients, having been corrected for α-Tubulin expression. AH+C+ patients have significantly lower DDAH II expression (P<0.01) and significantly higher PRMT-1 (P<0.01) expression.

DDAH II and PRMT-1 expression: Hepatic DDAH II expression (corrected for α-tubulin expression) was significantly lower (P<0.01) in the 4 AH+C+ patients in whom it was measured, as compared with 4 AH−C+ patients. In contrast, the expression of PRMT-1 was significantly increased in the livers' of AK+C+ patients (P<0.01) as shown in FIG. 7. PRMT-1 data for 7 patients is shown due to limited homogenate extracted from 1 AH−C+ patient to allow adequate gel loading.

Discussion

The results of this study show that patients with alcoholic cirrhosis with superimposed inflammation (AH+C+) proven histologically, and with elevated pro-inflammatory cytokines and SIRS components, have higher hepatic venous pressure gradients compared to patients with only cirrhosis (AH−C+). We extend previous observations of increased free circulating ADMA in decompensated cirrhosis[27] with the new additional finding of increased plasma and hepatic tissue ADMA in inflammatory AH+C+ patients compared to AH−C+, and demonstrate an association between increased ADMA and elevated portal pressure. Furthermore, our results demonstrate significantly lower ADMA and SDMA levels in survivors of decompensated cirrhosis, with SDMA also discriminating between survivors and non-survivors in the sub-group of inflammatory AH+C+ patients, in whom death is associated primarily with renal failure. When current validated scoring systems (Child-Pugh, DF and MELD) used to determine early outcome (in-patient mortality) or need for intervention in alcoholic hepatitis were applied to our cohort of patients, their predictive utility was limited. Circulating levels of ADMA, SDMA or the sum of these dimethylarginines (DAS) predicted those patients that were at risk of dying. Our results confirm previous reports that AH+C+ patients have significantly elevated plasma levels of TNFα, TNF-RI and RII compared with AH−C+ patients[21]. Inflammation, modulated through TNFα, is believed to be important in alcohol induced liver injury[28, 29] and its inhibition in animal models of alcoholic injury, significantly attenuates hepatic inflammation.[30] Furthermore, recent animal model data also suggests that additional inflammation may be important in the increased intrahepatic resistance in cirrhosis, giving rise to elevated portal pressure.[29] Thus, portal pressure in portal hypertensive animals and humans is reduced by interventions directed at mediators of inflammation such as treatment with thalidomide[31,32], and TNFα monoclonal antibodies[29] Our recent observation of a marked reduction in portal pressure in patients with cirrhosis who had superimposed alcoholic hepatitis, treated with an anti-TNFα monoclonal antibody, may support the hypothesis of a relationship between inflammation and factors modulating intravascular tone.[33]

There is general agreement in the literature that increased intrahepatic resistance in cirrhosis is contributed to by reduced local NO availability, secondary to decreased hepatic eNOS activity.[5, 6] ADMA is a competitive, endogenous inhibitor of eNOS produced during proteolysis,[11] and it has been suggested that the liver is an important site of ADMA metabolism.[13] Elevated ADMA has been shown to be associated with endothelial dysfunction in numerous conditions,[34-36] whilst increased urinary excretion of ADMA has been described in patients with chronic active hepatitis.[37] Recently, ADMA was found to be elevated in end-stage cirrhotics compared to healthy controls[27] and in liver failure patients prior to orthotopic liver transplantation, the levels falling significantly, post transplantation.[15] These studies imply that with progression of liver disease and portal hypertension, ADMA rises, and that after liver transplantation there is a rapid decline, suggesting a correction of the derangement in ADMA metabolism associated with a reduction in inflammatory indices, documented post transplantation.[38] In this study, we demonstrate significantly increased plasma and hepatic tissue levels of ADMA in AH+C+ patients with superimposed hepatic inflammation, compared to AH−C+ patients. The effects of inflammation appear to be above and beyond those expected for alcoholic cirrhosis alone[14]. This data would support a hypothesis that following an increase in hepatic inflammatory mediators, there is an alteration in hepatic ADMA metabolism or/and generation.

ADMA homeostasis is maintained by its metabolism through the enzyme DDAH, which is particularly abundant in the liver and kidney.[12, 39] DDAH activity has been shown to be reduced by inflammatory stimuli such as TNFα.[17] It follows that when levels of TNFα are markedly increased, as seen in AH+C+ patients, one might expect higher liver ADMA levels through impaired metabolism, and that this in turn may decrease local hepatic NOS activity. This assertion is supported in part by the observation of increased hepatic tissue ADMA coupled with decreased liver DDAH II protein expression (the most abundant subtype of DDAH found in the liver) in AH+C+ patients in this study, in whom HVPG was significantly increased.

An alternative explanation for our observation of increased ADMA in AH+C+ patients, is through increased ADMA production. ADMA is generated by the action of PRMTs, a family of enzymes that methylate the side-chain nitrogen of arginine within proteins.[40] Several types of PRMT have been described with Type I being responsible for the generation of $N^G$-monomethyl-L-arginine (L-NMMA) and ADMA, and Type II, L-NMMA and symmetric dimethylarginine (SDMA). Upon proteolysis, which is increased in hyper metabolic states such as cirrhosis and inflammation,[41] significant amounts of ADMA are generated[42]. The rate of ADMA and SDMA generation is thus likely to be dependent on the presence and activity of PRMTs and the rate of protein breakdown. In keeping with this, we observed an increase in expression of PRMT-1 in AH+C+ patients in whom there is increased inflammation, compared to AH−C+ patients. This observation is further supported by data from studies on human endothelial cells exposed to oxidised LDL-cholesterol, in which up-regulated ADMA release is associated with increased PRMT expression[43].

Although our study was neither powered nor aimed to look at the role of the dimethylarginines in determining survival, one of the most important findings to emerge from this study was the association of elevated ADMA and SDMA levels with in-hospital mortality in the whole group of alcoholic cirrhotic patients (25%) and specifically, in AH+C+ patients, in whom the mortality was 44%, in keeping with previous published series.[44, 45] Current scoring systems predicting outcome in alcoholic hepatitis are centred on biochemical (bilirubin, prothrombin time and creatinine) and clinical variables (degree of ascites and encephalopathy) and do not specifically factor in the significant changes in pro-inflammatory state or marked hemodynamic changes that are associated with this condition.[26, 46, 47]

In this study we identify the potential use of dimethylarginine levels as measurable biological markers (with minimal inter-assay variability), that may predict early in-patient mortality with a better sensitivity (73%) and specificity (83%) than currently used prognostic scores. Our data also suggests a further temporal increase in dimethylarginine levels in those with poor outcome but firm conclusions on the discriminatory value of repeated measurements are limited by the small number of patients studied. It is possible that ADMA levels partly reflect the inflammatory state in AH in which vascular dysfunction occurs, including within the renal circulatory bed.[48] Increasing ADMA has been associated with a decreased effective renal plasma flow and increased renovascular resistance,[49] which would lead to increased retention of SDMA. Indeed, SDMA has recently been shown to be elevated in hepatorenal syndrome patients compared to patients with cirrhosis without renal failure.[50] A combined dimethylarginine (DAS) score thus factors in both inflammation and incipient renal dysfunction (the main cause of mortality in our AH+C+ patient cohort) and might explain the better predictive utility of this score identified in our study.

In conclusion, we observed that AH+C+ patients have a more marked elevation in HVPG, which is associated with an increase in plasma and hepatic tissue ADMA. The increased ADMA in AH+C+ patients may result from both decreased breakdown (decreased hepatic DDAH) or/and increased production (increased PRMT expression and/or proteolysis). Elevated dimethylarginine levels may be an important biological marker of deleterious outcome in alcoholic hepatitis but further studies in appropriate models are required to determine if ADMA is causally involved.

Example 2

Patients Who Die of Alcoholic Liver Disease have a Significantly Increased IMA:Albumin Ratio Methods Method of assessment for an IMA:albumin ratio: Abbott Aeroset Bromocresol Purple (BCP) test is used for the measurement of serum albumin (Duly et al; J Clin Pathol 2003). The concentration of ischemia modified serum albumin can be determined by the addition of a known amount of Co(II) to a serum specimen and measurement of the unbound Co(II) by a colorimetric assay using dithiothreitol (DTT) (Bhagavan, N V; Clin Chem 2003 and Bar-Or D; Eur J Biochem 2001). An inverse relationship thus exists between the amount of albumin bound cobalt and the intensity of the colour formation. In brief: All reactions are carried out in 1.5 ml Eppendorfs at room temperature. 200 µL of patient serum is added to 50 µL of a solution of 1 g/L of cobalt chloride, followed by vigorous mixing, and a 10 minute incubation. DTT (50 µL of a 1.5 g/L solution) is then added and mixed. After a 2-min incubation, 1.0 mL of a 9.0 g/L solution of NaCl is added. The absorbance of assay mixtures is read at 470 nm with a Hewlett Packard 8452A Diode Array Spectrophotometer. A reference sample is prepared similarly with the exclusion of DTT. All chemicals, including cobalt chloride and DTT, purchased from Sigma-Aldrich.

Results

Development of a new biomarker: "DASIMAR": Given the varying levels of albumin in liver patients determined partly by nutrition and largely by residual liver synthetic function, we have modified the application of the albumin-cobalt binding assay to factor in a ratio of IMA to native albumin in the serum—a serum IMA:albumin ratio, or "IMAR". Data in a series of 52 decompensated patients with alcoholic liver disease suggest that patients who die have a significantly increased IMA:albumin ratio (P<0.01). Furthermore, as with the DAS value, there is a suggestion that IMAR may reflect inflammatory status and there-by the underlying pathological evolution of the disease. Using receiver operator curves to predict mortality, the area under the curve was found to be 0.73 (±0.06) for the cohort studied, suggesting that IMAR may be a useful predictive test of mortality in these patients.

Discussion

Figure 10:
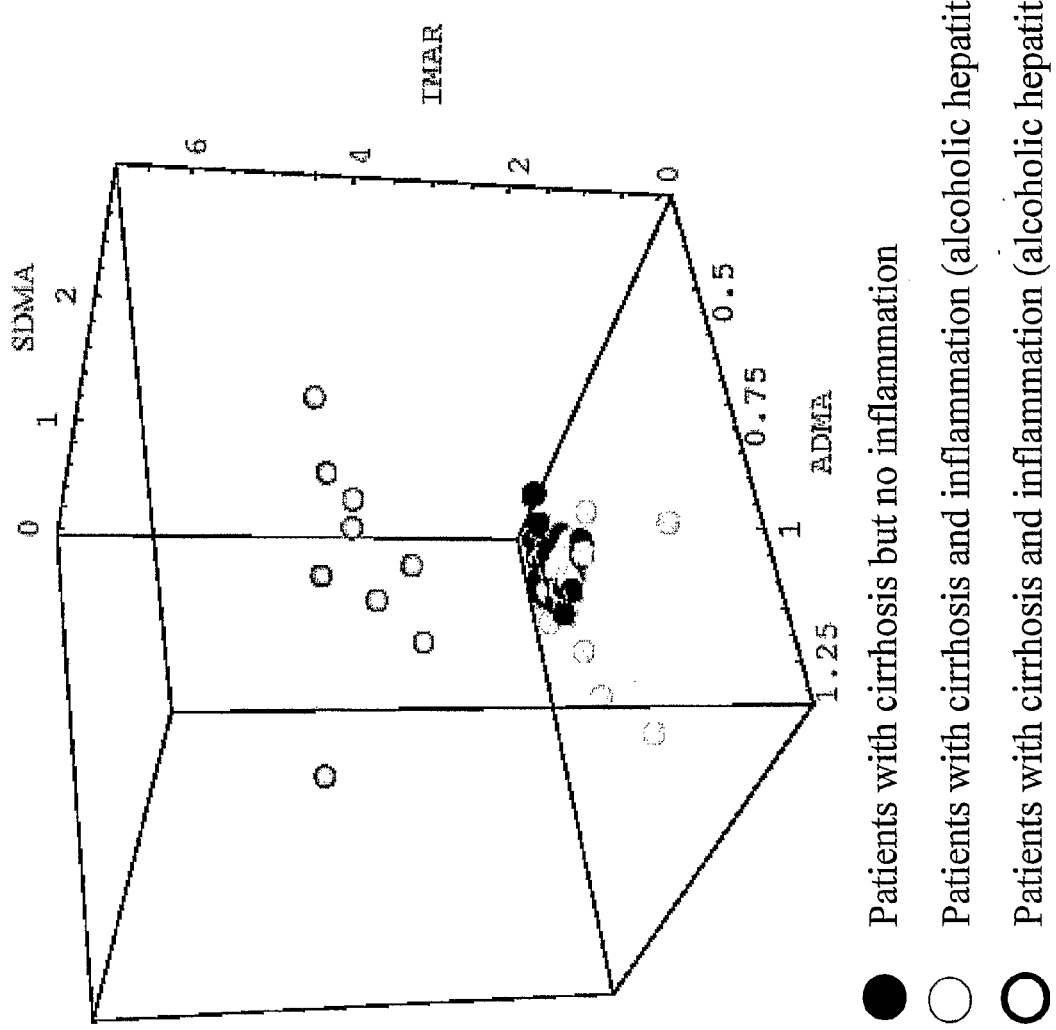
FIG. 10 shows the mathematical representation of all 3 components of the DASIMAR score (namely ADMA, SDMA, and IMAR) and clearly demonstrates the rationale for combining DAS and the IMAR scores to identify which susceptible patients are unlikely to survive. In the figure, the mid-grey dots (seen at higher valves on the IMAR axis) reveal the mathematical plane showing patients with alcoholic patients who die, clearly distinguishable from survivors and those with cirrhosis alone.

Despite both DAS and IMAR being suggestive of markers for disease progression and outcome, we found that combining a Dimethylarginine Score (DAS—see Example 1) with IMAR as a combined biomarker, improved the predictive utility of poor outcome, with an AUROC of 0.91 ((±0.04) with 95% confidence intervals of 0.81-0.99, and a sensitivity of 74% and specificity of 92%. This provides an excellent predictive utility to assess mortality risk. (FIGS. 9 and 10), whilst also reflecting worsening organ failure and inflammation, elements of the pathophysiology of liver failure, that may be targeted by specific interventions such as albumin dialysis and therapies to reduce inflammation. DASIMAR could thus potentially also be used to monitor response to intervention.

Example 3

IMAR, DAS and DASIMAR to Predict Survival in a Rodent Liver Failure Model

Rats were treated with an agent known to cause liver injury, galactosamine (Sigma, Poole UK), by intra-peritoneal injection (IP) at 1 g/kg (n=22) followed 24 hours later by a further challenge in a subgroup with lipopolysaccharide (LPS—*Klebsiella pneumonia*, n=11) to simulate additional infection/inflammation administered IP at 1 mg/kg. Blood samples were then obtained immediately prior to death.

Those animals receiving the challenge at 24 hours all incurred mortality by 6 hours, as compared to rats receiving galactosamine alone or sham animals which received a similar dose of LPS.

Figure 11:
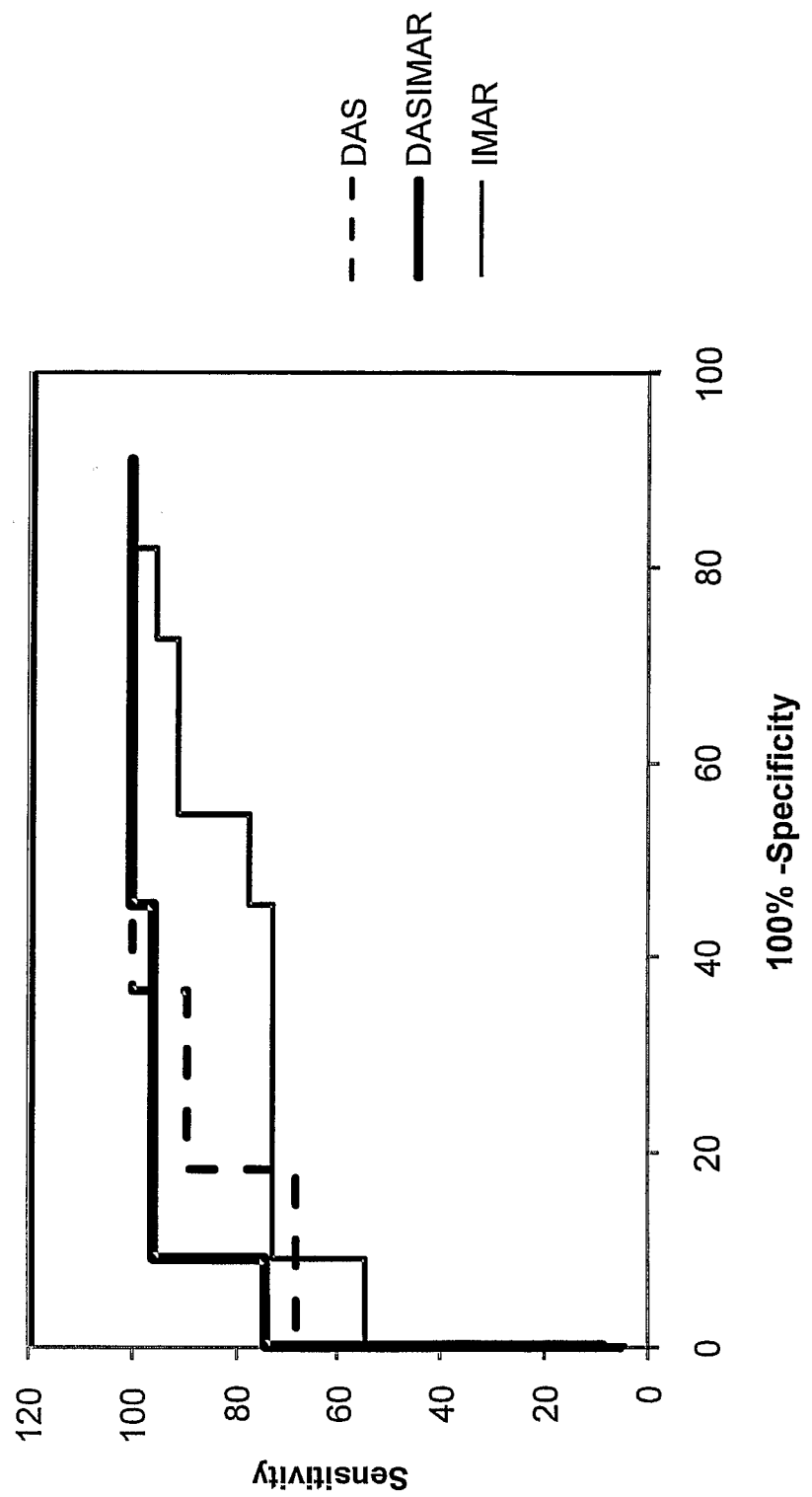
FIG. 11 shows the ROC curves for IMAR, DAS and DASIMAR obtained from studies performed on rats treated with galactosamine (Sigma, Poole UK) by intra-peritoneal injection (IP) at 1 g/kg (n=22) followed 24 hours later by a further challenge in a subgroup with lipopolysaccharide (LPS— *Klebsiella pneumonia*, n=11) administered IP at 1 mg/kg.

Measures of ADMA, SDMA, and IMAR were taken using the same methods described in the previous Examples. As with the data from human patients, it was seen that DASIMAR is a much better predictor of mortality (AUROC of 0.96) than DAS or IMAR alone (see FIG. 11). Indeed, in this model, DASIMAR has a high sensitivity (96%) and specificity (91%) in predicting outcome, highlighting the effect of combining DAS and IMAR components and emphasizing the utility of this score in different models of liver disease and in the context of sepsis.

|  | AUROC | Standard error of mean | Sensitivity % | Specificity % |
|---|---|---|---|---|
| DASIMAR | 0.96 | 0.03 | 96 | 91 |
| DAS | 0.92 | 0.05 | 89 | 82 |
| IMAR | 0.82 | 0.07 | 73 | 91 |

TABLE 1

Baseline characteristics for all patients studied and their sub-classification into patients with alcoholic hepatitis (AH+ C+) and cirrhosis with no inflammation (AH−C+)

|  | All Patients (n = 52) | Alcoholic Hepatitis (AH+C+, n = 27) | Cirrhosis Only (AH− C+, n = 25) |
|---|---|---|---|
| Age (years) | 50 [32-69] | 47 [32-69] ns | 51 [38-67] |
| Bilirubin (µmol/L) [3-17] | 169 ± 26 | 291 ± 38 *** | 56 ± 13 |
| Prothrombin (secs) [10-12] | 15.6 ± 0.7 | 18 ± 1 ** | 13.4 ± 0.6 |
| ALT (U/L) [8-50] | 55 ± 9 | 60 ± 15 ns | 47 ± 9 |
| Creatinine (µmol/L) [66-112] | 76.5 ± 9.7 | 92.5 ± 11 * | 59.8 ± 5 |
| Pugh Score | 10 ± 0.3 | 11.5 ± 0.3 *** | 8.4 ± 0.4 |
| MELD Score | 7.4 ± 1.7 | 15 ± 2.3 *** | 0.26 ± 1.4 |
| HVPG (mmHg) [<5] | 19 ± 1 | 22 ± 1.9 ** | 15.5 ± 1.6 |
| CRP (mg/L) [0-5] | 33.5 ± 6.5 | 50 ± 7 *** | 17 ± 3 |
| WBC (×10$^9$/L) [3-10] | 10.2 ± 1.4 | 14.3 ± 1.6 *** | 6.4 ± 0.5 |
| SIRS [0] | 0.9 ± 0.2 | 1.6 ± 0.4 *** | 0.3 ± 0.1 |

TABLE 1-continued

Baseline characteristics for all patients studied and their sub-classification into patients with alcoholic hepatitis (AH+ C+) and cirrhosis with no inflammation (AH−C+)

| | All Patients (n = 52) | Alcoholic Hepatitis (AH+C+, n = 27) | Cirrhosis Only (AH− C+, n = 25) |
|---|---|---|---|
| TNFα (pg/ml) [0-5] | 21 ± 11 | 46 ± 20 ** | 4 ± 0.5 |
| TNFR1 (ng/ml) [0-1.6] | 726 ± 76 | 885 ± 93 ** | 455 ± 74 |
| TNFR2 (ng/ml) [0-3.5] | 1237 ± 141 | 1798 ± 128 *** | 759 ± 136 |
| IL-6 (pg/ml) [0-5] | 29.5 ± 9.6 | 55.7 ± 19 * | 9.3 ± 2 |

TABLE 2

Outcome characteristics amongst studied patients

| | Alcoholic hepatitis Deaths (n = 12) | Alcoholic hepatitis Discharged (n = 15) | Cirrhosis Only Discharged (n = 24) |
|---|---|---|---|
| Renal Failure | 8 | 1 | 0 |
| Gastrointestinal Bleed | 2 | 2 | 1 |
| Infection | 6 (2 with SBP) | 6 | 5 |
| Pugh score | 11.9 ± 0.5 | 11.1 ± 0.4 | 8.4 ± 0.4 *** |
| MELD | 16.2 ± 3.9 | 14.2 ± 3.1 | 0.7 ± 1.7 *** |
| Discriminant Function | 53 ± 13 | 41 ± 6 | — |

*** P < 0.001: Alcoholic Cirrhosis compared with Alcoholic hepatitis patients discharged from hospital

TABLE 3

Comparison of prognostic scores with dimethylarginine levels to predict outcome in all studied alcoholic cirrhosis patients and in a subgroup with alcoholic hepatitis using receiver operator curves

| | Dimethylarginine level | | | |
|---|---|---|---|---|
| Scoring system | Cut-off value (% Sensitivity; Specificity) | AU ROC | Cut-off value (% Sensitivity; Specificity) | AU ROC |
| Pugh | 10.5 (63; 75) | 0.81 ± 0.07 | 11.5 (60; 64) | 0.65 ± 0.11 |
| DF | 36 (76; 73) | 0.78 ± 0.08 | 39 (53; 70) | 0.55 ± 0.13 |
| MELD | 10.3 (74; 73) | 0.76 ± 0.08 | 18.9 (60; 40) | 0.53 ± 0.12 |
| ADMA | 0.57 (74; 77) | 0.83 ± 0.08 | 0.65 (73; 75) | 0.74 ± 0.09 |
| SDMA | 0.7 (77; 85) | 0.87 ± 0.06 | 0.89 (73; 67) | 0.82 ± 0.08 |
| DAS (AH+C+) | 1.23 (77; 92) | 0.9 ± 0.05 | 1.52 (73; 83) | 0.85 ± 0.07 |
| | All Patients | | Alcoholic Hepatitis | |

DAS (Dimethylarginine Score) = Sum of ADMA and SDMA
AUROC (area under the curve) ± SEM
Sensitivity and specificity, respectively, at each Cut-off value is specified in parenthesis References 1. Tome S, Lucey M R. Review article: current management of alcoholic liver disease. Aliment Pharmacol Ther 2004; 19:707-14.
2. Duvoux C, Radier C, Roudot-Thoraval F, Maille F, Anglade M C, Van Nhieu J T, Rosa I, Hospitel S, Abd-Alsamad I, Sitruk V, Seror O, Ziol M, Blondon H, Dhumeaux D, Richardet J P. Low-grade steatosis and major changes in portal flow as new prognostic factors in steroid-treated alcoholic hepatitis. Hepatology 2004; 40:1370-8.
3. Ripoll C, Banares R, Rincon D, Catalina M V, Lo Iacono O, Salcedo M, Clemente G, Nunez O, Matilla A, Molinero L M. Influence of hepatic venous pressure gradient on the prediction of survival of patients with cirrhosis in the MELD Era. Hepatology 2005; 42:793-801.
4. Wiest R, Groszmann R J. The paradox of nitric oxide in cirrhosis and portal hypertension: too much, not enough. Hepatology 2002; 35:478-91.
5. Gupta T K, Toruner M, Chung M K, Groszmann R J. Endothelial dysfunction and decreased production of nitric oxide in the intrahepatic microcirculation of cirrhotic rats. Hepatology 1998; 28:926-31.
6. Rockey D C, Chung J J. Reduced nitric oxide production by endothelial cells in cirrhotic rat liver: endothelial dysfunction in portal hypertension. Gastroenterology 1998; 114: 344-51.
7. Fiorucci S, Antonelli E, Brancaleone V, Sanpaolo L, Orlandi S, Distrutti E, Acuto G, Clerici C, Baldoni M, Del Soldato P, Morelli A. NCX-1000, a nitric oxide-releasing derivative of ursodeoxycholic acid, ameliorates portal hypertension and lowers norepinephrine-induced intrahepatic resistance in the isolated and perfused rat liver. J Hepatol 2003; 39:932-9.
8. Van De Casteele M, Omasta A, Janssens S, Roskams T, Desmet V, Nevens F, Fevery J. In vivo gene transfer of endothelial nitric oxide synthase decreases portal pressure in anaesthetised carbon tetrachloride cirrhotic rats. Gut 2002; 51:440-445.
9. Shah V, Chen A F, Cao S, Hendrickson H, Weiler D, Smith L, Yao J, Katusic Z S. Gene transfer of recombinant endothelial nitric oxide synthase to liver in vivo and in vitro. Am J Physiol Gastrointest Liver Physiol 2000; 279:G1023-30.
10. Morales-Ruiz M, Cejudo-Martn P, Fernandez-Varo G, Tugues S, Ros J, Angeli P, Rivera F, Arroyo V, Rodes J, Sessa W C, Jimenez W. Transduction of the liver with activated Akt normalizes portal pressure in cirrhotic rats. Gastroenterology 2003; 125:522-31.
11. Leiper J, Vallance P. Biological significance of endogenous methylarginines that inhibit nitric oxide synthases. Cardiovasc Res 1999; 43:542-8.
12. MacAllister R J, Parry H, Kimoto M, Ogawa T, Russell R J, Hodson H, Whitley G S, Vallance P. Regulation of nitric oxide synthesis by dimethylarginine dimethylaminohydrolase. Br J Pharmacol 1996; 119:1533-40.
13. Nijveldt R J, Teerlink T, Siroen M P, van Lambalgen A A, Rauwerda J A, van Leeuwen P A. The liver is an important organ in the metabolism of asymmetrical dimethylarginine (ADMA). Clin Nutr 2003; 22:17-22.
14. Lluch P, Torondel B, Medina P, Segarra G, Del Olmo J A, Serra M A, Rodrigo J M. Plasma concentrations of nitric oxide and asymmetric dimethylarginine in human alcoholic cirrhosis. J Hepatol 2004; 41:55-9.
15. Siroen M P, Warle M C, Teerlink T, Nijveldt R J, Kuipers E J, Metselaar H J, Tilanus H W, Kuik D J, van der Sijp J R, Meijer S, van der Hoven B, van Leeuwen P A. The transplanted liver graft is capable of clearing asymmetric dimethylarginine. Liver Transpl 2004; 10:1524-30.
16. Nijveldt R J, Teerlink T, Van Der Hoven B, Siroen M P, Kuilc D J, Rauwerda J A, van Leeuwen P A. Asymmetrical dimethylarginine (ADMA) in critically ill patients: high plasma ADMA concentration is an independent risk factor of ICU mortality. Clin Nutr 2003; 22:23-30.
17. Ito A, Tsao P S, Adimoolam S, Kimoto M, Ogawa T, Cooke J P. Novel mechanism for endothelial dysfunction: dysregulation of dimethylarginine dimethylaminohydrolase. Circulation 1999; 99:3092-5.
18. MacSween R N, Burt A D. Histologic spectrum of alcoholic liver disease. Semin Liver Dis 1986; 6:221-32.

19. Bone R C, Sibbald W J, Sprung C L. The ACCP-SCCM consensus conference on sepsis and organ failure. Chest 1992; 101:1481-3.
20. Owen L J, Wear J E, Keevil B G. Validation of a liquid chromatography tandem mass spectrometry assay for serum creatinine and comparison with enzymatic and Jaffe methods. Ann Clin Biochem 2006; 43:118-23.
21. Tilg H, Jalan R, Kaser A, Davies N A, Offner F A, Hodges S J, Ludwiczek O, Shawcross D, Zoller H, Alisa A, Mookerjee R P, Graziadei I, Datz C, Trauner M, Schuppan D, Obrist P, Vogel W, Williams R. Anti-tumor necrosis factor-alpha monoclonal antibody therapy in severe alcoholic hepatitis. J Hepatol 2003; 38:419-25.
22. Gornall A G. Determination of serum proteins by means of the biuret reaction. J. Biol. Chem 1949; 177:751-766.
23. Infante-Rivard C, Esnaola S, Villeneuve J P. Clinical and statistical validity of conventional prognostic factors in predicting short-term survival among cirrhotics. Hepatology 1987; 7:660-4.
24. Kamath P S, Wiesner R H, Malinchoc M, Kremers W, Therneau T M, Kosberg C L, D'Amico G, Dickson E R, Kim W R. A model to predict survival in patients with end-stage liver disease. Hepatology 2001; 33:464-70.
25. Brunt E M, Janney C G, Di Bisceglie A M, Neuschwander-Tetri B A, Bacon B R. Nonalcoholic steatohepatitis: a proposal for grading and staging the histological lesions. Am J Gastroenterol 1999; 94:2467-74.
26. Maddrey W C, Boitnott J K, Bedine M S, Weber F L, Jr., Mezey E, White R I, Jr. Corticosteroid therapy of alcoholic hepatitis. Gastroenterology 1978; 75:193-9.
27. Tsikas D, Rode I, Becker T, Nashan B, Klempnauer J, Frolich J C. Elevated plasma and urine levels of ADMA and 15(S)-8-iso-PGF2alpha in end-stage liver disease. Hepatology 2003; 38:1063-4.
28. Khoruts A, Stahnke L, McClain C J, Logan G, Allen J I. Circulating tumor necrosis factor, interleukin-1 and interleukin-6 concentrations in chronic alcoholic patients. Hepatology 1991; 13:267-76.
29. Lopez-Talayera J C, Merrill W W, Groszmann R J. Tumor necrosis factor alpha: a major contributor to the hyperdynamic circulation in prehepatic portal-hypertensive rats. Gastroenterology 1995; 108:761-7.
30. Iimuro Y, Gallucci R M, Luster M I, Kono H, Thurman R G. Antibodies to tumor necrosis factor alfa attenuate hepatic necrosis and inflammation caused by chronic exposure to ethanol in the rat. Hepatology 1997; 26:1530-7.
31. Austin A S, Mahida Y R, Clarke D, Ryder S D, Freeman J G. A pilot study to investigate the use of oxpentifylline (pentoxifylline) and thalidomide in portal hypertension secondary to alcoholic cirrhosis. Aliment Pharmacol Ther 2004; 19:79-88.
32. Lopez-Talayera J C, Cadelina G, Olchowski J, Merrill W, Groszmann R J. Thalidomide inhibits tumor necrosis factor alpha, decreases nitric oxide synthesis, and ameliorates the hyperdynamic circulatory syndrome in portal-hypertensive rats. Hepatology 1996; 23:1616-21.
33. Mookerjee R P, Sen S, Davies N A, Hodges S, Williams R, Jalan R. TNF is an important mediator of portal and systemic hemodynamic derangements in alcoholic hepatitis. Gut 2003; 52:1182-87.
34. Achan V, Broadhead M, Malaki M, Whitley G, Leiper J, MacAllister R, Vallance P. Asymmetric dimethylarginine causes hypertension and cardiac dysfunction in humans and is actively metabolized by dimethylarginine dimethylaminohydrolase. Arterioscler Thromb Vasc Biol 2003; 23:1455-9.
35. Zoccali C, Bode-Boger S, Mallamaci F, Benedetto F, Tripepi G, Malatino L, Cataliotti A, Bellanuova I, Fermo I, Frolich J, Boger R. Plasma concentration of asymmetrical dimethylarginine and mortality in patients with end-stage renal disease: a prospective study. Lancet 2001; 358:2113-7.
36. Savvidou M D, Hingorani A D, Tsikas D, Frolich J C, Vallance P, Nicolaides K H. Endothelial dysfunction and raised plasma concentrations of asymmetric dimethylarginine in pregnant women who subsequently develop pre-eclampsia. Lancet 2003; 361:1511-7.
37. Carnegie P R, Fellows F C, Symington G R. Urinary excretion of methylarginine in human disease. Metabolism 1977; 26:531-7.
38. Jalan R, Pollok A, Shah S H, Madhavan K, Simpson K J. Liver derived pro-inflammatory cytokines may be important in producing intracranial hypertension in acute liver failure. J Hepatol 2002; 37:536-8.
39. Ogawa T, Kimoto M, Sasaoka K. Occurrence of a new enzyme catalyzing the direct conversion of NG,NG-dimethyl-L-arginine to L-citrulline in rats. Biochem Biophys Res Commun 1987; 148:671-7.
40. McBride A E, Silver P A. State of the arg: protein methylation at arginine comes of age. Cell 2001; 106:5-8.
41. Marliss E B, Chevalier S, Gougeon R, Morais J A, Lamarche M, Adegoke O A, Wu G. Elevations of plasma methylarginines in obesity and ageing are related to insulin sensitivity and rates of protein turnover. Diabetologia 2006; 49:351-9.
42. Inoue R, Miyake M, Kanazawa A, Sato M, Kalcimoto Y. Decrease of 3-methylhistidine and increase of NG,NG-dimethylarginine in the urine of patients with muscular dystrophy. Metabolism 1979; 28:801-4.
43. Boger R H, Sydow K, Borlak J, Thum T, Lenzen H, Schubert B, Tsikas D, Bode-Boger S M. LDL cholesterol upregulates synthesis of asymmetrical dimethylarginine in human endothelial cells: involvement of S-adenosylmethionine-dependent methyltransferases. Circ Res 2000; 87:99-105.
44. Akriviadis E, Botla R, Briggs W, Han S, Reynolds T, Shakil O. Pentoxifylline improves short-term survival in severe acute alcoholic hepatitis: a double-blind, placebo-controlled trial. Gastroenterology 2000; 119:1637-48.
45. Carithers R L, Jr., Herlong H F, Diehl A M, Shaw E W, Combes B, Fallon H J, Maddrey W C. Methylprednisolone therapy in patients with severe alcoholic hepatitis. A randomized multicenter trial. Ann Intern Med 1989; 110:685-90.
46. Forrest E H, Evans C D, Stewart S, Phillips M, Oo Y H, McAvoy N C, Fisher N C, Singhal S, Brind A, Haydon G, O'Grady J, Day C P, Hayes P C, Murray L S, Morris A J. Analysis of factors predictive of mortality in alcoholic hepatitis and derivation and validation of the Glasgow alcoholic hepatitis score. Gut 2005; 54:1174-9.
47. Dunn W, Jamil L H, Brown L S, Wiesner R H, Kim W R, Menon K V, Malinchoc M, Kamath P S, Shah V. MELD accurately predicts mortality in patients with alcoholic hepatitis. Hepatology 2005; 41:353-8.
48. Mookerjee R P D N, Hodges S J, Dalton R N, Williams R, Jalan R. Hepatic inflammation increases portal pressure through inhibition of eNOS activity—potential mechanisms. Gut 2006:Abstract.
49. Kielstein J T, Tsikas D, Fliser D. Effects of asymmetric dimethylarginine (ADMA) infusion in humans. Eur J Clin Pharmacol 2006; 62 Suppl 13:39-44.
50. Lluch P, Mauricio M D, Vila J M, Segarra G, Medina P, Del Olino J A, Rodrigo J M, Serra M A. Accumulation of symmetric dimethylarginine in hepatorenal syndrome. Exp Biol Med (Maywood) 2006; 231:70-5.

The invention claimed is:

1. A method for assessing liver function in an individual, wherein the method comprises
   (a) measuring the level of asymmetric dimethylarginine (ADMA) and symmetric dimethylarginine (SDMA) in the individual;
   (b) measuring the ratio of ischemia modified albumin : albumin (IMAR) in the individual; and
   (c) comparing the level of step (a) and the ratio of step (b) with the combined level of ADMA and SDMA and the IMAR in an individual not suffering from liver disease or in an individual who is a survivor of liver disease, wherein an increase in the combined level of ADMA and SDMA and an increase in IMAR in the individual, as compared to the combined level of ADMA and SDMA and IMAR in an individual not suffering from liver disease or in an individual who is a survivor of liver disease, is indicative of an increased risk of mortality in the individual.

2. A method according to claim 1, wherein the individual is suffering from liver failure.

3. A method according claim 2, wherein the individual is suffering from chronic liver failure, acute-on-chronic liver failure or acute liver failure.

4. A method according to claim 1, wherein the individual is suffering from alcoholic liver disease.

5. A method according to claim 4, wherein the individual is suffering from cirrhosis or cirrhosis and/or alcoholic hepatitis.

6. A method according to claim 1, wherein the method further comprises determining one or more additional liver disease prognostic scores.

7. A method according to claim 6, wherein the one or more additional liver disease prognostic scores is one or more of the Child-Pugh scoring system, West Haven Criteria, Glasgow Coma Scale, modified Child-Pugh scoring system, sequential organ failure assessment (SOFA), Model for End-Stage Liver Disease (MELD) or Acute Physiology and Chronic Health Evaluation II.

8. A method according to claim 1, wherein steps (a) and (b) of claim 1 are performed on a sample obtained from the individual.

9. A method according to claim 8, wherein the sample is a plasma sample or a hepatic tissue sample.

10. A method for assessing liver function in an individual, wherein the method comprises
   (a) obtaining a sample from the individual;
   (b) measuring the level of one or more methylarginines selected from the group consisting of asymmetric dimethylarginine (ADMA) and symmetric dimethylarginine (SDMA) in the sample;
   (c) measuring the ratio of ischemia modified albumin: albumin (IMAR) in the sample; and
   (d) comparing the levels of ADMA, SDMA and IMAR of steps (a) and (b) with the levels of ADMA, SDMA and IMAR measured at an earlier time in the same individual, wherein a change in a combined level of ADMA and SDMA and IMAR in the individual, as compared to a combined level of ADMA, SDMA and IMAR measured at an earlier time in the same individual is indicative of an increased risk of mortality in the individual.

* * * * *